United States Patent
Gibson et al.

(10) Patent No.: US 12,336,761 B2
(45) Date of Patent: Jun. 24, 2025

(54) MULTI-LASER EYE TRACKING SYSTEM THAT SCANS LIGHT FROM LASER LIGHT SOURCES DURING RESPECTIVE PERIODS OF TIME

(71) Applicant: Microsoft Technology Licensing, LLC, Redmond, WA (US)

(72) Inventors: Gregory Theodore Gibson, Seattle, WA (US); Joshua Owen Miller, Woodinville, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 18/489,804

(22) Filed: Oct. 18, 2023

(65) Prior Publication Data
US 2024/0041321 A1 Feb. 8, 2024

Related U.S. Application Data

(62) Division of application No. 16/600,441, filed on Oct. 11, 2019, now Pat. No. 11,826,103.

(51) Int. Cl.
*A61B 3/113* (2006.01)
*A61F 9/008* (2006.01)

(52) U.S. Cl.
CPC .............. *A61B 3/113* (2013.01); *A61F 9/008* (2013.01); *A61F 2009/00846* (2013.01); *A61F 2009/00872* (2013.01)

(58) Field of Classification Search
CPC ...................... A61B 3/113; A61F 9/008; A61F 2009/00846; A61F 2009/00872; G02B 26/0833; G02B 26/101; G02B 27/0093; G06F 3/013; G06V 20/20; G06V 40/19
See application file for complete search history.

(56) References Cited

U.S. PATENT DOCUMENTS

2017/0205876 A1* 7/2017 Vidal .................... G01S 17/87

OTHER PUBLICATIONS

Communication under Rule 71(3) received in European Application No. 20775495.3, mailed on Jul. 9, 2024, 8 pages.
Decision to Grant pursuant to Article 97(1) received in European Application No. 20775495.3, mailed on Oct. 31, 2024, 02 pages.

* cited by examiner

*Primary Examiner* — David D Davis
(74) *Attorney, Agent, or Firm* — Wade IP Law PLLC

(57) ABSTRACT

Techniques are described herein that are capable of tracking an eye of a user using multiple lasers. Light from the lasers is scanned across respective partially overlapping portions of a region that includes an eye of a user during respective time periods. Portion(s) of the light that are reflected from the eye are detected by respective photodetector(s). In an example implementation, a signal corresponding to the detected portion(s) is provided in a pixel of a frame buffer based at least in part on a current angle of a mirror used to scan the light across the region. In a second implementation, digital state(s) are provided based at least in part on difference(s) between a reference signal and signal(s) corresponding to the detected portion(s), and a time value indicating a time at which a glint is detected by a photodetector is provided when a digital state triggers an interrupt handler.

20 Claims, 11 Drawing Sheets

MULTI-LASER EYE TRACKING SYSTEM THAT SCANS LIGHT FROM LASER LIGHT SOURCES DURING RESPECTIVE PERIODS OF TIME

CROSS-REFERENCE TO RELATED APPLICATION(S)

This application is a division of U.S. patent application Ser. No. 16/600,441, filed Oct. 11, 2019 and entitled "Multi-Laser Eye Tracking System That Scans Light From Laser Light Sources During Respective Periods of Time," the entirety of which is incorporated by reference herein.

BACKGROUND

An eye tracking system is a system that is configured to track an eye with respect to a frame of reference. Tracking the eye typically includes determining location and/or movement (e.g., rotation) of the eye with respect to the frame of reference. For instance, the frame of reference may be a head in which the eye is located. Angles associated with the eye that are measured with reference to the head are referred to as "eye-in-head angles." Information regarding a direction in which the head is facing in a coordinate system (e.g., a three-dimensional coordinate system) may be combined with the eye-in-head angles to determine a direction of gaze of a user (i.e., the direction in which the user looks) in the coordinate system and/or a point of gaze of the user (i.e., a location at which the user looks) in the coordinate system.

SUMMARY

Various approaches are described herein for, among other things, tracking an eye of a user using multiple lasers. For instance, tracking the eye of the user may include determining location and/or movement of the eye. A laser is a device that emits light via optical amplification based on stimulated emission of radiation (e.g., electromagnetic radiation). The laser may be formed in a semiconductor chip. For instance, the laser may be formed as a waveguide on a semiconductor substrate of the semiconductor chip. A multi-laser eye tracking system may include one or more semiconductor chips, and each semiconductor chip may include one or more lasers. Each of the lasers in a multi-laser eye tracking system is capable of being controlled separately from the other lasers. For example, the lasers may be sequentially illuminated (a.k.a. activated). In accordance with this example, as illumination from an activated laser is swept out of a region of interest, the activated laser may be shut off and another laser, which is still in the region of interest, may be activated. Activating the lasers in this manner may increase "dwell" time in the region of interest for image capture and tracking while simultaneously decreasing the latency or effective frame rate in the region of interest.

In an example approach, light from multiple laser light sources is scanned across a region that includes an eye of a user. The laser light sources include at least a first laser light source and a second laser light source. First light from the first laser light source is scanned across a first portion of the region during a first period of time. Second light from the second laser light source is scanned across a second portion of the region during a second period of time that is different from the first period of time. The second portion of the region at least partially overlaps the first portion of the region. Portion(s) of the light that are reflected from an iris of the eye are detected by one or more respective photodetectors. Analog signal(s) are generated by the respective photodetector(s) based at least in part on the respective detected portion(s) of the light. A sum of the analog signal(s) that are generated by the respective photodetector(s) is converted to a digital signal. A current mirror scan angle of a scanning mirror that is used to scan the light from the laser light sources across the region is calculated. The digital signal is provided in a pixel of a frame buffer based at least in part on the current mirror scan angle.

In another example approach, light from multiple laser light sources is scanned across a region that includes a cornea of a user. The laser light sources include at least a first laser light source and a second laser light source. First light from the first laser light source is scanned across a first portion of the region during a first period of time. Second light from the second laser light source is scanned across a second portion of the region during a second period of time that is different from the first period of time. The second portion of the region at least partially overlaps the first portion of the region. Portion(s) of the light that are reflected from the cornea of the user at respective corresponding angle(s) are detected by respective photodetector(s). Current(s) are generated by the respective photodetector(s) based at least in part on the respective detected portion(s) of the light. The current(s) that are generated by the respective photodetector(s) are converted to respective voltage(s). The voltage(s) are compared to a reference voltage. Digital state(s) are provided based at least in part on respective difference(s) between the reference voltage and the respective voltage(s). A time value is provided when a digital state, which is included among the digital state(s), triggers an interrupt handler. The time value indicates a time at which a glint is detected by a photodetector.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Moreover, it is noted that the invention is not limited to the specific embodiments described in the Detailed Description and/or other sections of this document. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate embodiments of the present invention and, together with the description, further serve to explain the principles involved and to enable a person skilled in the relevant art(s) to make and use the disclosed technologies.

Figure 1:
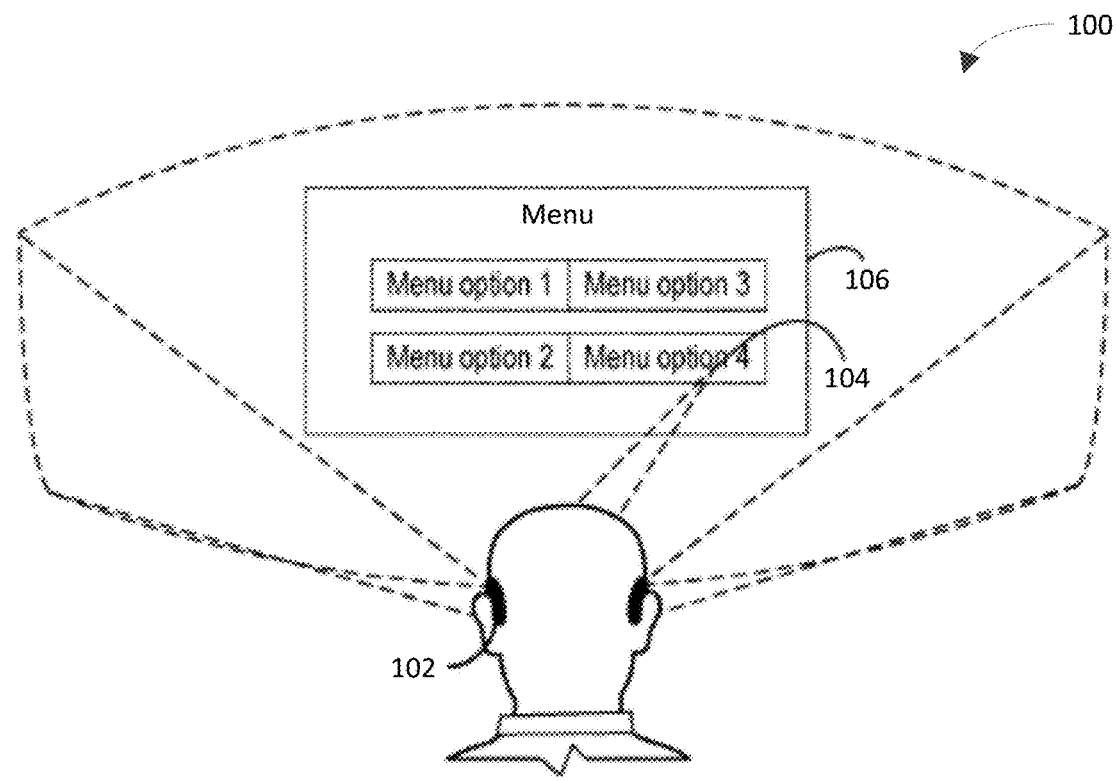
FIG. 1 shows an example scenario for use of eye tracking on a near-eye display device.

The features and advantages of the disclosed technologies will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

I. Introduction

The following detailed description refers to the accompanying drawings that illustrate exemplary embodiments of the present invention. However, the scope of the present invention is not limited to these embodiments, but is instead defined by the appended claims. Thus, embodiments beyond those shown in the accompanying drawings, such as modified versions of the illustrated embodiments, may nevertheless be encompassed by the present invention.

References in the specification to "one embodiment," "an embodiment," "an example embodiment," or the like, indicate that the embodiment described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it is submitted that it is within the knowledge of one skilled in the relevant art(s) to implement such feature, structure, or characteristic in connection with other embodiments whether or not explicitly described.

II. Example Embodiments

Example embodiments described herein are capable of tracking an eye of a user using multiple lasers. For instance, tracking the eye of the user may include determining location and/or movement of the eye. A laser is a device that emits light via optical amplification based on stimulated emission of radiation (e.g., electromagnetic radiation). The laser may be formed in a semiconductor chip. For instance, the laser may be formed as a waveguide on a semiconductor substrate of the semiconductor chip. A multi-laser eye tracking system may include one or more semiconductor chips, and each semiconductor chip may include one or more lasers. Each of the lasers in a multi-laser eye tracking system is capable of being controlled separately from the other lasers. For example, the lasers may be sequentially illuminated (a.k.a. activated). In accordance with this example, as illumination from an activated laser is swept out of a region of interest, the activated laser may be shut off and another laser, which is still in the region of interest, may be activated.

Example techniques described herein have a variety of benefits as compared to conventional techniques for tracking an eye of a user. For instance, the example techniques may be capable of increasing "dwell" time in a region of interest for image capture and tracking; decreasing the latency or effective frame rate in the region of interest; increasing an amount of information regarding the region of interest that is captured in each frame; and/or reducing an amount of time that is consumed to capture such information. The example techniques may increase efficiency of an eye tracking system. For instance, the example techniques may reduce a number of scans per frame that are not directed to the region of interest and increase a number of scans per frame that are directed to the region of interest. By utilizing multiple lasers to perform a scan during each frame, the example embodiments may increase efficiency of an eye tracking system. The example multi-laser eye tracking systems described herein may track an eye of a user more accurately than a conventional eye tracking system. Tracking the eye more accurately may increase user interaction performance (e.g., lead to an improved user experience). For instance, greater accuracy of the eye tracking may result in greater accuracy in other aspects of the user experience that are dependent on the eye tracking. The example techniques may provide a multi-laser eye tracking system that has a relatively small form factor, which may reduce cost of the eye tracking system and increase headroom in the eye tracking system. The example techniques may be more integrated and/or less obtrusive than conventional techniques. The example techniques may be capable of providing any the above-mentioned benefits simultaneously.

The example techniques described herein are applicable to any of a variety of applications and systems, including but not limited to augmented reality (AR) systems, virtual reality (VR) systems, foveated imaging systems, security systems, and medical diagnostic systems. For instance, a security system may utilize one or more of the techniques described herein to authenticate a user by analyzing the light that reflects from the iris of the user. A medical diagnostic system may utilize one or more of the techniques described herein to analyze biometrics of the user (e.g., images of the user's iris) for purposes of detecting a disease.

FIG. 1 shows an example scenario 100 for use of eye tracking on a near-eye display device 102. As shown in FIG. 1, the near-eye display device 102 is worn by a user. In one example, the near-eye display device 102 may be implemented as an augmented reality display device that utilizes a see-through display to superimpose virtual imagery over a real-world background being viewed, or may capture video of the real-world background and composite the video with virtual imagery for display. Leveraging existing image display system components for eye tracking may allow light from the eye tracking illumination sources to be presented to an eye of the user on a same or similar axis as that of the display imagery without impeding a view of a real world background. In another example, the near-eye display device 102 may be implemented as a virtual reality display device that displays fully virtual imagery.

As shown in FIG. 1, the user's gaze direction 104, as determined from eye tracking, may be used to detect a user input regarding a virtual menu 106 that is displayed by the near-eye display device 102 to appear at a distance in front of the user. Eye tracking may also be used for other human-computer interactions, such as visual attention analysis and foveated display.

The near-eye display device 102 may utilize laser light sources, one or more microelectromechanical systems (MEMS) mirrors, and potentially other optics (e.g. a waveguide) to produce and deliver an image to a user's eye. The near-eye display device 102 may leverage such existing display system components, which may help to reduce a number of components used in manufacturing the near-eye display device 102. For example, by adding an appropriately configured infrared laser for eye illumination, an existing MEMS mirror system used for scanning image production also may be used to scan the light from the eye tracking illumination sources across the user's eye.

The scanning system of the near-eye display device 102 may take any suitable form. For example, the scanning system may include one or more mirrors that are controlled to direct light from light sources (e.g., laser beams) toward a region that includes the eye. The mirror(s) may move over the course of a frame to control the location in the region toward which the light is directed. For example, the scanning system may include a fast scan MEMS mirror and a slow scan MEMS mirror. The fast scan MEMS mirror may oscillate about a first axis under resonance. The slow scan MEMS mirror may oscillate about a second axis that is perpendicular to the first axis to scan linearly. In this manner, the fast scan MEMS mirror and the slow scan MEMS mirror can perform a raster scan of the light in the region. In another example, the scanning system may include a single mirror to scan the light in the region.

In some examples, the light may be delivered from the scanning system to the user's eye by a waveguide, as mentioned above. In other examples, another component, such as a see-through mirror positioned in front of the eye, may be used to direct light to the eye. In either instance, light may be directed to the eye without having to place a scanning system directly in front of the eye. The scanning system may be configured to over-scan the corneal region of the eye to accommodate for varying interpupillary distances, eyeball rotations, and eye reliefs across users.

Photodetectors such as photodiodes may be provided at suitable locations to capture specular reflections from the user's cornea for glint tracking and to capture diffusely scattered light for greyscale imaging. By analyzing attribute(s) of the reflected light (e.g., the specular reflections and/or the greyscale images), the location and/or direction of the eye may be determined.

Figure 2:
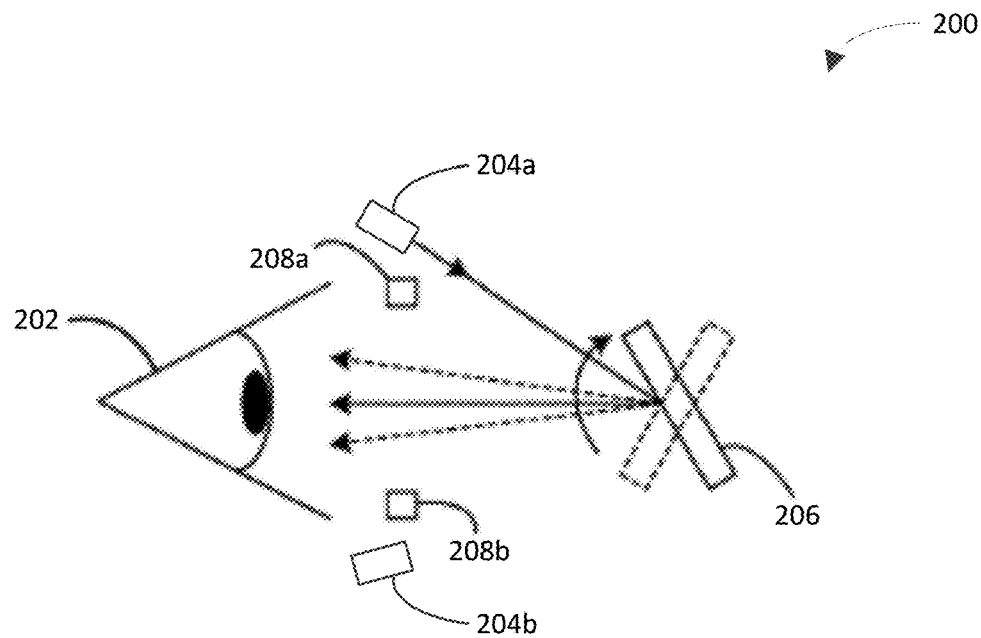
FIG. 2 is a schematic diagram of an example eye tracking system in accordance with an embodiment.

FIG. 2 is a schematic diagram of an example eye tracking system 200 in accordance with an embodiment. For instance, the eye tracking system 200 may be incorporated into a near-eye display system, such as the near-eye display device 102 shown in FIG. 1, for tracking an eye 202 of a user. The eye tracking system 200 includes light sources 204a and 204b, which may take the form of lasers, light-emitting diodes, or other suitable emitters. The light sources 204a and 204b may be infrared light source, ultraviolet light sources, or other suitable type of light sources. Two light sources 204a and 204b are shown in FIG. 2 for illustrative purposes and are not intended to be limiting. It will be recognized that the eye tracking system 200 may include any suitable number of light sources (e.g., 2, 3, 4, 5, and so on), so long as the eye tracking system 200 includes more than one light source.

The light sources 204a and 204b are sequentially illuminated (a.k.a. activated), such that the light emitted by the light sources 204a and 204b is sequentially received at a scanning MEMS mirror system 206. The scanning MEMS mirror system 206 scans the light from the light sources 204a and 204b across respective portions of a region that includes the eye 202. For instance, in response to the scanning MEMS mirror system 206 scanning the light emitted by the light source 204a across a first portion of the region, which includes an entirety of a region of interest that includes the eye or a portion thereof (e.g., the pupil or the cornea), the eye tracking system 200 may de-activate (a.k.a. discontinue illumination, turn off) the light source 204a and activate (e.g., initiate activation of) the light source 204b. The scanning MEMS mirror system 206 then scans the light emitted by the light source 204b across a second portion of the region, which includes the entirety of the region of interest. In response to the scanning MEMS mirror system 206 scanning the light emitted by the light source 204b across the second portion of the region, which includes the entirety of the region of interest, the eye tracking system 200 may de-activate the light source 204b and re-activate the light source 204a to perform one or more additional iterations of the scanning operations described above. Further detail regarding example techniques for using multiple lasers to track an eye of a user is provided below with reference to FIGS. 3-11 and 12A-12B.

The scanning mirror system 206 may include a single mirror that scans in two dimensions, or may include separate mirrors that each scan in one direction orthogonal to the direction of the other mirror. As the light is scanned across the eye 202, the light reflects from the eye 202 in directions based upon the angle at which the light is incident on the surface of the eye 202. The reflected light is detected via photodetectors 208a and 208b. In one example, the photodetectors 208a and 208b may be separately located photodiodes. In another example, the photodetectors 208a and 208b may take the form of a linear array. Two photodetectors 208a and 208b are shown in FIG. 2 for illustrative purposes and are not intended to be limiting. It will be recognized that the eye tracking system 200 may include any suitable number of photodetectors (e.g., 1, 2, 3, 4, 5, and so on). In some examples, the number of photodetectors present may depend on the eye tracking algorithm utilized by the eye tracking system 200.

As the light scans across the eye, each of the photodetectors 208a and 208b receives light that is scattered by the iris of the eye 202 and light that is specularly reflected from the cornea of the eye 202 at specific scanning system angles based upon the locations of the photodetectors 204a and 204b and the rotational position of the eye 202. Lower-intensity scattered light (e.g., reflected from the iris) is used to form a greyscale image of the scanned region of the eye 202 in a pupil location processing system, and higher-intensity specular reflections (e.g., reflected from the cornea) are utilized to determine glint locations in a glint location processing system. For pupil location processing, the signals from the photodetectors 208a and 208b may be sampled and computationally combined (e.g., summed) at each angular position of the scanning mirror system 206 to form a bitmap image for use in identifying a location of the pupil. Summing the signals from the photodetectors 208a and 208b may provide a higher signal-to-noise ratio than using a single sensor for detecting scattered light. Specular reflections may be processed by recording a time stamp and an angular position at which the higher intensity of the specular reflection is received at that photodetector, and changes in the relative locations of the glints may be used to provide information regarding eye rotation. Eye rotation information from glint tracking may be used to control a frame rate of the pupil location processing system in some examples.

Figure 3:
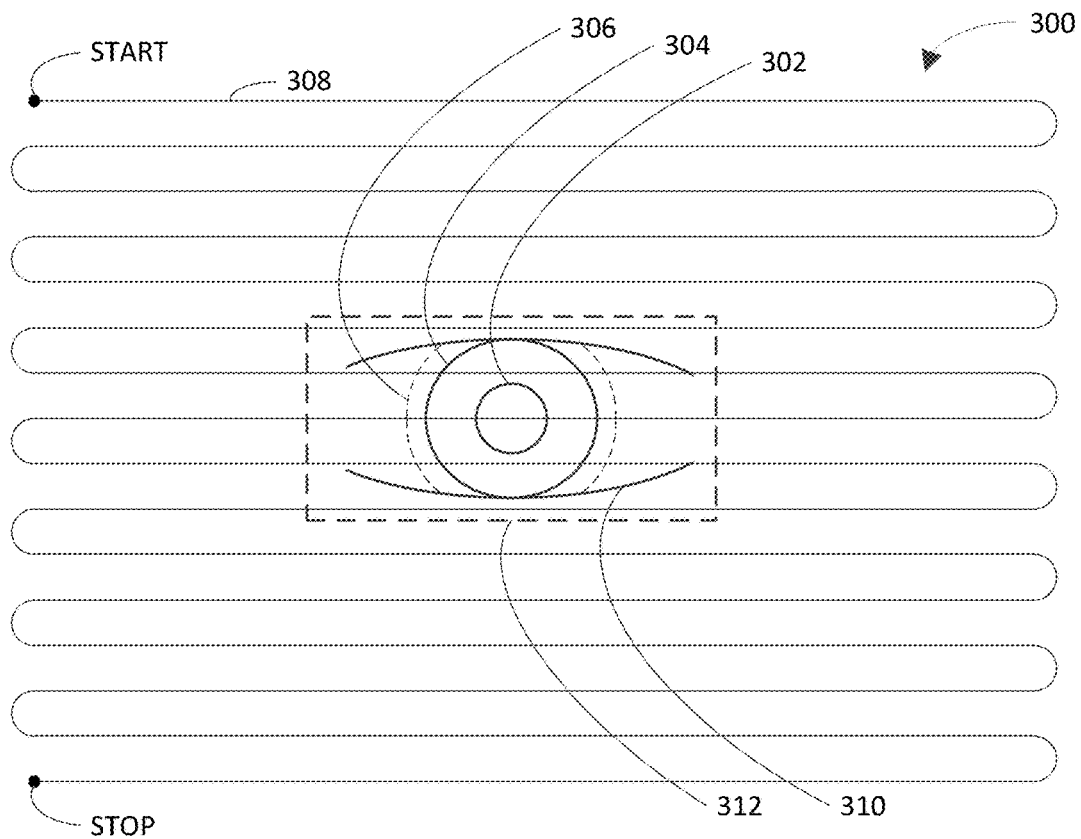
FIG. 3 illustrates a single-laser scan in a region that includes an eye of a user.

FIG. 3 illustrates a single-laser scan 300 in a region that includes an eye 310 of a user. As shown in FIG. 3, light that is emitted from a single laser is scanned across the region along a path 308 from a starting point (labeled "START") to a stopping point (labeled "STOP") for each frame. The path 308 is shown to form a raster pattern that includes sixteen horizontal lines for non-limiting, illustrative purposes. It will be recognized that the raster pattern may include any suitable number of horizontal lines. The region includes a region of interest 312, which includes the eye 310. The eye 310 is shown to include a pupil 302, an iris 304, and a cornea 306. It will be recognized that the region of interest 312 need not necessarily include an entirety of the eye 310. Because the scanned light is from a single laser, the region of interest 312 is scanned once per frame. In the embodiment of FIG. 3, a substantial proportion of the path 308 does not fall within the region of interest 312. Accordingly, the dwell time in the region of interest 312 may be relatively low, and/or the latency or effective frame rate in the region of interest 312 may be relatively high.

Figure 4:
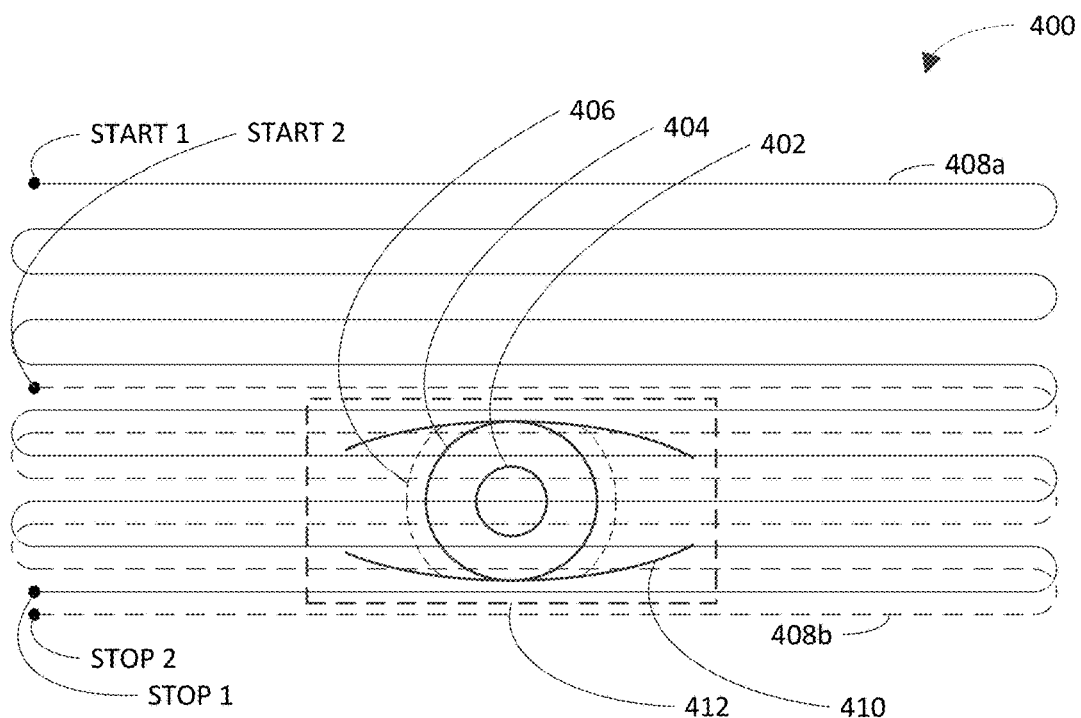
FIG. 4 illustrates a multi-laser scan in a region that includes an eye of a user in accordance with an embodiment.

FIG. 4 illustrates a multi-laser scan 400 in a region that includes an eye 410 of a user in accordance with an embodiment. As shown in FIG. 4, light that is emitted from a first laser is scanned across a first portion of the region along a first path 408a from a first starting point (labeled "START1") to a first stopping point (labeled "STOP1") for each frame. Light that is emitted from a second laser is scanned across a second portion of the region along a second path 408b from a second starting point (labeled "START2") to a second stopping point (labeled "STOP2") for each frame. Each of the first and second paths 408a and 408b is shown to form a respective raster pattern for non-limiting, illustrative purposes. For instance, the first path 408a is shown to form a raster pattern that includes ten horizontal lines for non-limiting, illustrative purposes, and the second path 408b is shown to form a raster pattern that includes six horizontal lines for non-limiting, illustrative purposes. It will be recognized that each of the raster patterns may include any suitable number of horizontal lines. The region includes a region of interest 412, which includes the eye 410. The eye 410 is shown to include a pupil 402, an iris 404, and a cornea 406. It will be recognized that the region of interest 412 need not necessarily include an entirety of the eye 410.

The scan of the light from the second laser (i.e., the second scan) is initiated after the scan of the light from the first laser (i.e., the first scan) is stopped. The second scan is spatially and temporally delayed with respect to the first scan, as depicted in FIG. 4. For instance, it can be seen in FIG. 4 that after the first scan has passed through the region of interest 412 and stopped, the second scan has not yet reached the region of interest 412. Thus, performing the first scan and the second scan sequentially enables the region of interest 412 to be scanned twice per frame. Accordingly, the dwell time in the region of interest 412 of FIG. 4 may be greater than (e.g., twice) the dwell time in the region of interest 312 of FIG. 3, and/or the latency or effective frame rate in the region of interest 412 of FIG. 4 may be less than (e.g., half) the latency or effective frame rate in the region of interest 312 of FIG. 3. It will be recognized that light emitted from more than two lasers (e.g., 3, 4, 5, 6, or more lasers) may be scanned across respective portions of the region to further increase dwell time in the region of interest and/or to further decrease latency or effective frame rate in the region of interest. For instance, each additional laser may contribute toward increasing dwell time and/or decreasing latency or effective frame rate, so long as the portion of the region across which light from the laser is scanned includes the region of interest.

Figure 5:
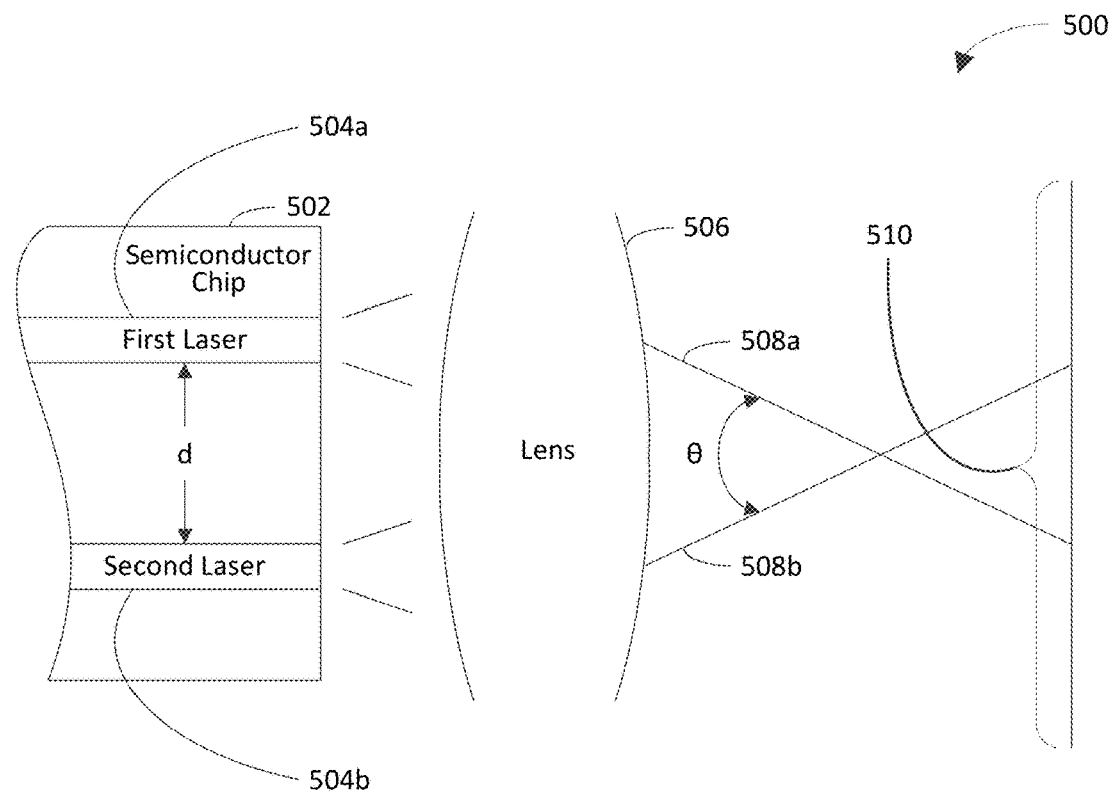
FIG. 5 illustrates an optical assembly configured to focus light from multiple laser light sources in a region in accordance with an embodiment.

FIG. 5 illustrates an optical assembly 500 configured to focus light 508a and 580b from multiple laser light sources 504a and 504b in a region 510 in accordance with an embodiment. A semiconductor chip 502 includes the first and second laser light sources 504a and 504b for non-limiting, illustrative purposes. It will be recognized that the first and second laser light sources 504a and 504b may be included in respective semiconductor chips. A lens 506 focuses light that is emitted by the first and second laser light sources 504a and 504b toward the region 510. An extent to which a scan of the light emitted from the second laser light source 504b (i.e., the second scan) in the region 510 is spatially delayed with respect to a scan of the light emitted from the first laser light source 504a (i.e., the first scan) in the region 510 is based on an angle, θ, between a path 508a of the light emitted by the first laser light source 504a and a path 508b of the light emitted by the second laser light source 504b. The angle, θ, is based on a spacing, d, between the first and second laser light sources 504a and 504b. As the spacing, d, increases, the angle, θ, increases. As the spacing, d, decreases, the angle, θ, decreases. Accordingly, a relatively greater spacing, d, results in a relatively greater spatial delay of the second scan with respect to the first scan. A relatively lesser spacing, d, results in a relatively lesser spatial delay of the second scan with respect to the first scan. In an example embodiment, a spacing between the first and second laser light sources 504a and 504b is greater than or equal to a threshold distance. For instance, the threshold distance may be 0.08 millimeters (mm), 0.1 mm, 0.12 mm, 0.15 mm, or 0.2 mm.

Figure 6:
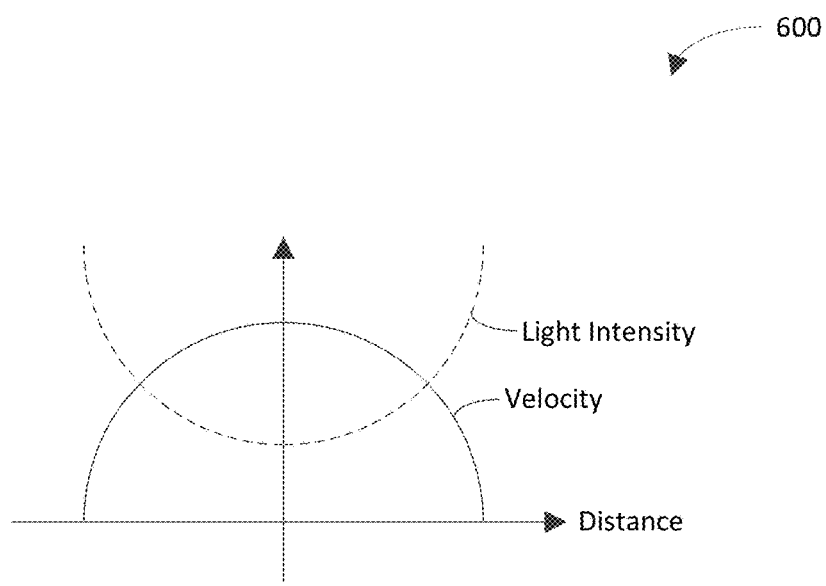
FIG. 6 shows example plots of light intensity and velocity with respect to distance in accordance with an embodiment.

FIG. 6 shows example plots 600 of light intensity and velocity with respect to distance in accordance with an embodiment. The plot of velocity indicates that as the light that is emitted by a laser is scanned across a region, the velocity decreases toward the outer edges of the region. For instance, a scanning mirror that reflects the light toward the region stops (i.e., velocity becomes zero) at the outer edges of the region to reverse direction. When the scanning mirror stops, the intensity of the light at that point increases, as reflected by the plot of light intensity. At each point along a path of the scan in the region, a relatively greater velocity contributes to a relatively lesser light intensity at that point, and a relatively lesser velocity contributes to a relatively greater intensity at that point. Accordingly, the example multi-laser eye tracking systems described herein may compensate for non-linearity of light intensity across the region. For instance, the example multi-laser eye tracking systems may increase the intensity of the light in the scan as the velocity increases and/or decrease the intensity of the light in the scan as the velocity decreases.

Figure 7:
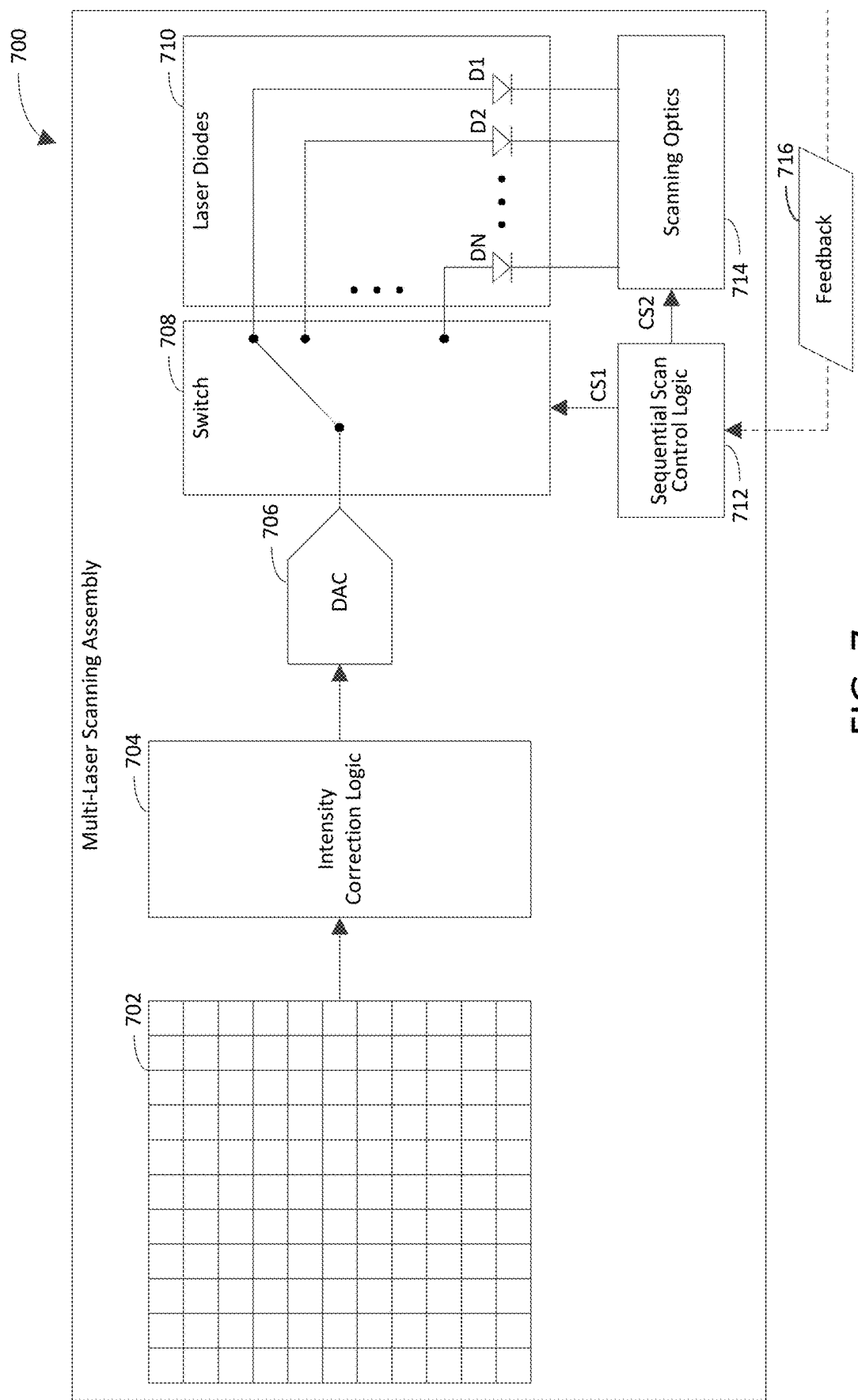
FIG. 7 is a block diagram of an example multi-laser scanning assembly in accordance with an embodiment.

FIG. 7 is a block diagram of an example multi-laser scanning assembly 700 in accordance with an embodiment. As shown in FIG. 7, the multi-laser scanning assembly 700 includes a correction matrix 702, intensity correction logic 704, a digital-to-analog converter (DAC) 706, a switch 708, laser diodes 710 (labeled D1-DN), sequential scan control logic 712, and scanning optics 714. The correction matrix 702 indicates an amount of light intensity correction that is to be applied to the scan for each point in the region. For instance, the correction matrix 702 may be configured to compensate for the non-linearity of light intensity across the region that is based on the non-linear velocity curve described above with reference to FIG. 6. It will be recognized that the correction matrix 702 may be configured to compensate for other light intensity variations associated with the scan in addition to or in lieu of those associated with the non-linear velocity curve.

The intensity correction logic 704 is configured to establish a value of a digital drive signal corresponding to each point (e.g., display pixel) in the region based at least in part on the amount of light intensity correction that is indicated for that point by the correction matrix 702. For instance, the intensity correction logic 704 may adjust (e.g., increase or decrease) the value associated with each point from a default value to an adjusted value based at least in part on the amount of light intensity correction that is indicated for that point.

The DAC 706 is configured to convert the digital drive signal corresponding to each point in the region to a respective analog signal. The switch 708 is configured to selectively couple the DAC 706 to one of the laser diodes 710 at a time based on a first control signal CS1 that is received from the sequential scan control logic 712. By selectively coupling the DAC 706 to one of the laser diodes 710 at a time, the switch 708 enables the analog signal corresponding to each point in the region to illuminate the laser diode to which the DAC 706 is coupled at that time. For instance, the switch 708 may couple the DAC 706 to a first diode D1 for a first subset of the points in the region based on the first control signal CS1 controlling the switch 708 to do so. The switch 708 may couple the DAC 706 to a second diode D2 for a second subset of the points in the region based on the first control signal CS1 controlling the switch 708 to do so, and so on.

The laser diodes 710 are configured to emit light in response to activation by the switch 708. Each of the laser diodes 710 is activated (i.e., turned on) as a result of the switch 708 coupling the DAC 706 to the respective laser diode. Each of the laser diodes 710 is de-activated (i.e., turned off) as a result of the switch 708 not coupling the DAC 706 to the respective laser diode (e.g., de-coupling the DAC 706 from the respective laser diode). A spacing between adjacent laser diodes may be greater than or equal to a threshold spacing. For instance, the threshold spacing may be 0.08 mm, 0.1 mm, 0.12 mm, 0.15 mm, or 0.2 mm.

The sequential scan control logic 712 is configured to generate the first control signal to control operation of the switch 708. By configuring the first control signal CS1 to cause the switch 708 to selectively couple the DAC 706 to the laser diodes 710 in a sequential manner, the sequential scan control logic 712 may cause the light emitted by each of the laser diodes 710 to be scanned across a respective portion of the region. For instance, the sequential scan control logic 712 may configure the first control signal CS1 to cause the switch 708 to couple the DAC 706 to a first laser diode D1 until the scan of the first laser diode D1 has passed through a region of interest in the region. For example, feedback 716 from a glint location processing system and/or a pupil location processing system (examples of which are discussed below with reference to FIG. 8) may indicate that the scan of the first laser diode D1 has passed through the region of interest. In accordance with this example, the feedback 716 may include information (e.g., a grayscale image value) regarding a point in the region to which the scan of the first laser diode D1 is directed and/or information regarding other point(s) in the region through which the scan has passed. In further accordance with this example, the sequential scan control logic 712 may determine that the scan of the first laser diode D1 has passed through the region of interest based at least in part on the information regarding the point in the region to which the scan is directed and/or the information regarding the other point(s) in the region through which the scan has passed. The sequential scan control logic 712 may then configure the first control signal CS1 to cause the switch 708 to de-activate the first laser diode D1 and to activate a second laser diode D2. For instance, the sequential scan control logic 712 may configure the first control signal CS1 to cause the switch 708 to de-couple the DAC 706 from the first laser diode D1 and then couple the DAC 706 to the second laser diode D2 until the scan of the second laser diode D2 has passed through the region of interest, and so on until the switch 708 has sequentially connected the DAC 706 to each of the laser diodes 710 to enable the scan of each laser diode to pass through the region of interest. The sequential scan control logic 712 may de-activate each laser diode and activate the next sequential laser diode based on the feedback 716 from the glint location processing system and/or the pupil location processing system indicating that the scan of the respective laser diode has passed through the region of interest.

The sequential scan control logic 712 is further configured to generate a second control signal CS2 to control the scanning optics 714. For example, the scanning optics 714 may include mirror(s), and the sequential scan control logic 712 may generate the second control signal CS2 to control movement of the mirror(s). In accordance with this example, the sequential scan control logic 712 may generate the second control signal CS2 to move the mirror(s) such that the mirror(s) reflect the light that is emitted by the laser diodes 710 across the respective portions of the region.

The scanning optics 714 are configured to scan the light that is emitted from the laser diodes 710 across the region based on the second control signal CS2. For instance, the scanning optics 714 may include mirror(s). Each mirror may be configured to oscillate about one or more axes based on the second control signal CS2. For example, the mirror(s) may include a fast scan MEMS mirror configured to rotate (e.g., oscillate) about a first axis and a slow scan MEMS mirror configured to rotate about a second axis that is orthogonal to the first axis. In accordance with this example, the fast scan MEMS mirror and the slow scan MEMS mirror may operate collaboratively to scan the light from the laser diodes 710 across respective portions of the region (e.g., in a raster pattern) based on the second control signal CS2.

It will be recognized that the multi-laser scanning assembly 700 may not include all of the components shown in FIG. 7. Furthermore, the multi-laser scanning assembly 700 may include components in addition to or in lieu of those shown in FIG. 7.

Figure 8:
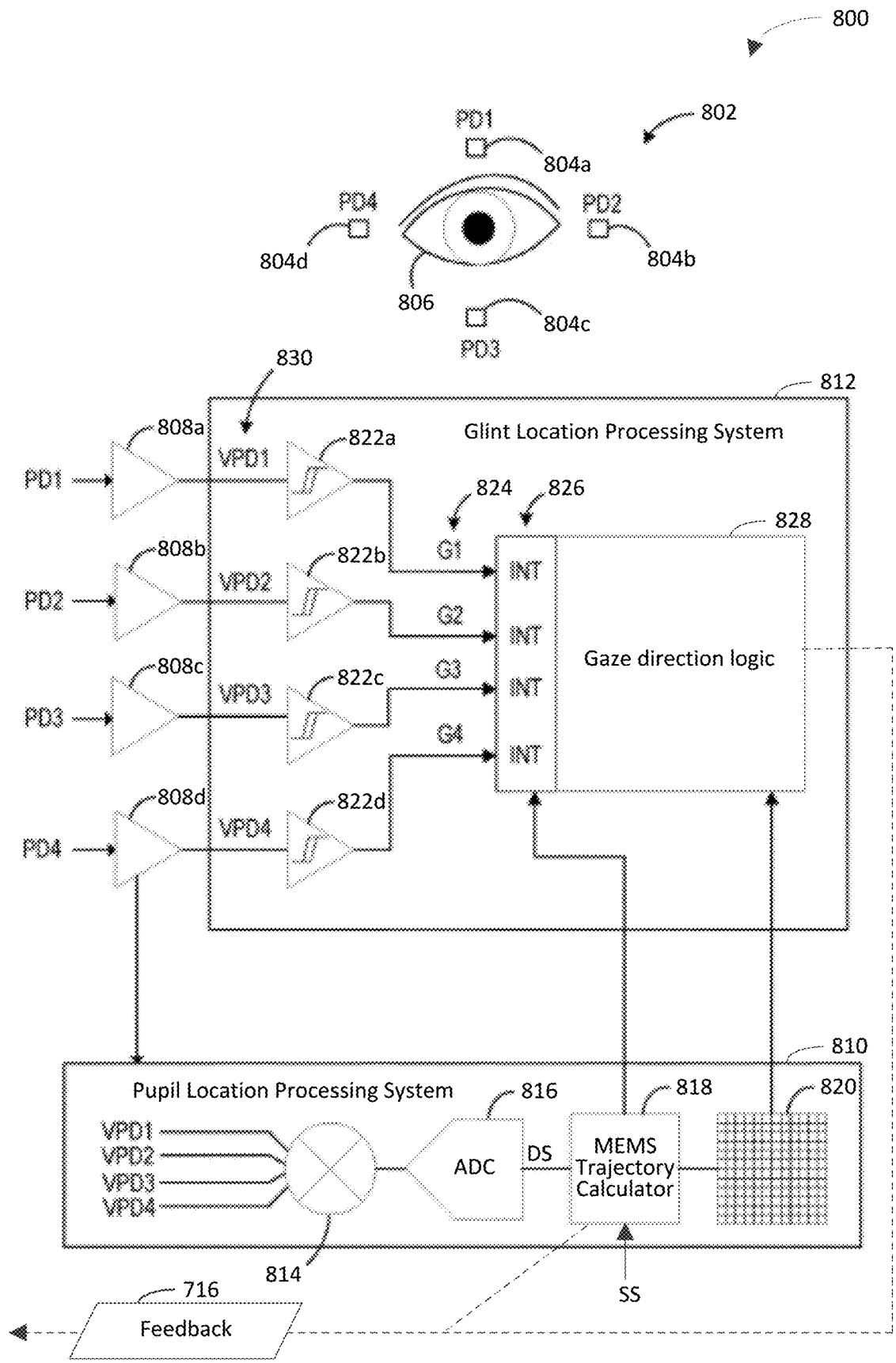
FIG. 8 is a block diagram of example processing pipelines in an eye tracking system.

FIG. 8 is a block diagram of example processing pipelines 800 in an eye tracking system. Functionality of the processing pipelines 800 is described with regard to a single sample period (a.k.a. frame) and in the context of an eye tracking system 802 having four photodetectors 804a-804d for non-limiting, illustrative purposes. Each of the photodetectors 804a-804d is configured to detect light reflected by the eye 806. For instance, the light may be received at the eye 806 from a multi-laser scanning assembly, such as the multi-laser scanning assembly 700 shown in FIG. 7. The photodetectors 804a-804d generate respective analog currents PD1, PD2, PD3, and PD4 based on the reflected light that is detected at the respective photodetectors 804a-804d. The current-to-voltage converters 808a-808d convert the respective analog currents PD1, PD2, PD3, and PD4 into respective analog voltages VPD1, VPD2, VPD3, and VPD4. The current-to-voltage converters 808a-808d may be transimpedance amplifiers (TIAs), though the scope of the example embodiments is not limited in this respect. The analog voltages VPD1, VPD2, VPD3, and VPD4 are provided to a pupil location processing system 810 and a glint location processing system 812 for processing.

The pupil location processing system 810 includes a summing junction 814, an analog-to-digital converter (ADC) 816, a MEMS trajectory calculator 818, and frame buffer 820. The summing junction 814 sums the analog voltages VPD1, VPD2, VPD3, and VPD4 to provide a summed analog voltage, which increases the signal amplitude and reduces noise proportionally to the square root of the sum. The ADC 816 converts the summed analog voltage to a summed digital signal DS representing intensity values for reflected light detected for the sample period. The MEMS trajectory calculator 818 receives synchronized signals SS from the MEMS scanning mirror. The synchronized signals SS indicate a current scan x-position and y-position of the scanning mirror during the sample period. The MEMS trajectory calculator 818 calculates the current scan angle based on the synchronized signals SS. Based on the scan angle, the MEMS trajectory calculator 818 stores the summed digital signal DS generated by the ADC 816 in a corresponding pixel in the frame buffer 820 for that particular angle. Thus, as the mirror rotates and light is scanned across the eye 806, a determined summed digital signal DS is stored in the appropriate pixel for each different scan angle, eventually resulting in a full frame buffer with each pixel storing a detected intensity signal, forming a greyscale image. The formed greyscale image may then be analyzed to determine a location of a pupil in the greyscale image. In this example, as four photodetectors are used, the greyscale image would have four bright spots in the image, corresponding to locations of respective glints.

The MEMS trajectory calculator 818 may provide feedback 716 (or a portion thereof), indicating whether a scan of a laser diode during the sample period has passed through a region of interest. For instance, the feedback 716 may include information regarding the current scan angle, the summed digital signal (a.k.a. detected intensity signal) corresponding to the current scan angle, summed digital signals corresponding to other scan angles, other information regarding the greyscale image, etc.

More accurate locations of the glints may be determined by the glint location processing system 812. The glint location processing system 812 includes comparators 822a-822d, interrupt handlers 826, and gaze direction logic 828. The comparators 822a-822d compare the respective analog voltages VPD1, VPD2, VPD3, and VPD4 that are received from the respective current-to-voltage converters 808a-808d to respective reference voltages and provide respective digital states 824 (labeled "G1", "G2", "G3", and "G4") based on the comparisons. Any two or more of the reference voltages may be the same or different. For example, each of the digital states G1-G4 may take the form an output bit, such that when the received analog voltage exceeds a reference voltage, the output bit changes from a first state to a second state. The reference voltage at each of the comparators 822a-822d may be set, for example, to half of the total glint amplitude or to any other suitable value. Next, each of the digital states G1-G4 is received at an interrupt handler 826. When a digital signal (e.g., a corresponding output bit) changes from the first state to the second state, the corresponding interrupt handler 826 may be triggered to store a current time value (e.g., a clock state of an operating clock). The output results in a generated list of glint events with corresponding time values. The glint location processing system 812 may utilize a MEMS trajectory calculator, similar to the MEMS trajectory calculator 818 that is included in the pupil location processing system 810, to associate each time value with a current MEMS scan angle. The gaze direction logic 828 may then calculate the location of a glint using the known mirror scan angle at the time that the glint was received by a corresponding photodetector. Thus, glint locations may be determined using comparator outputs without performing image analysis, which may allow glint tracking to be performed in a power-efficient manner. The gaze direction logic 828 may use an eye tracking algorithm to determine an eye gaze direction based on the glint locations and the pupil location, as determined from the greyscale image.

The gaze direction logic 828 may provide feedback 716 (or a portion thereof), indicating whether a scan of a laser diode has passed through a region of interest. For instance, the feedback 716 may include information regarding glint location(s) and/or pupil location(s).

Pupil location processing may consume more power than glint location processing at a same frame rate. As such, the pupil location processing system 810 may be configured to be inactive or operate at a lower frame rate until a threshold magnitude of eye rotation is detected via the glint location processing system 812 system. The eye tracking algorithm may use a most recent pupil image stored in the frame buffer 820 for gaze determination until eye rotation of sufficient magnitude is determined from the glint location processing system 812 to trigger operation of (or a higher frame rate of operation for) the pupil location processing system 812. This may help the eye tracking system to conserve power.

It will be recognized that the pipelines 800 may not include all of the components shown in FIG. 8. Furthermore, the pipelines 800 may include components in addition to or in lieu of those shown in FIG. 8.

Figure 9:
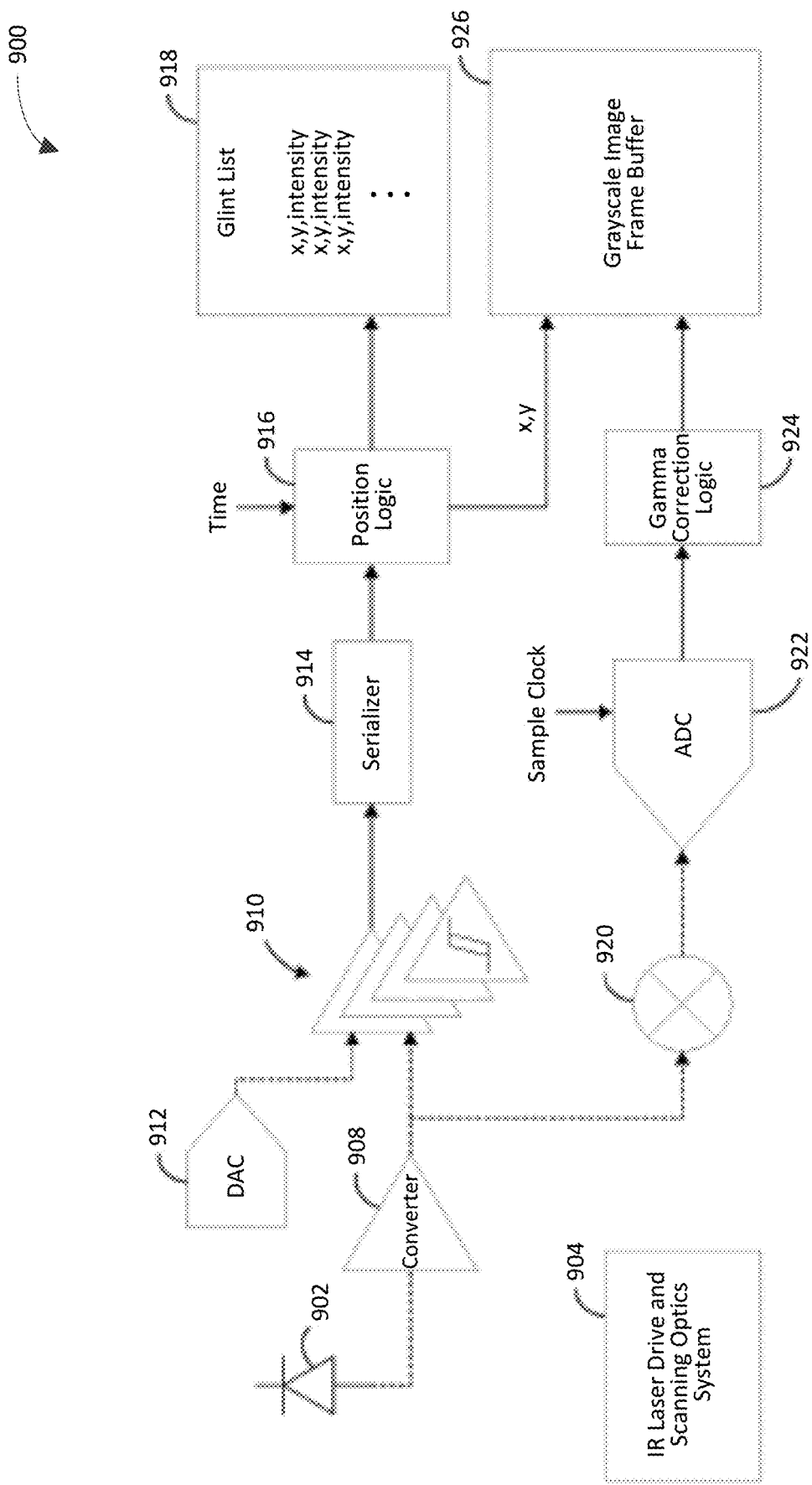
FIG. 9 is a block diagram of example processing pipelines in another eye tracking system.

FIG. 9 is a block diagram of example processing pipelines 900 in another eye tracking system. The processing pipelines 900 are described and illustrated in the context of a single photodetector 902 for non-limiting, illustrative purposes. It will be understood that the system and processes described may apply to each of a plurality of photodetectors in the eye tracking system. As shown in FIG. 9, the pipelines 900 include the photodetector 902, an infrared (IR) laser drive and scanning optics system 904, a current-to-voltage converter 908, comparators 910, a digital-to-analog converter (DAC) 912, a serializer 914, position logic 916, a summing junction 920, an analog-to-digital converter (ADC) 922, gamma correction logic 924, and a grayscale image frame buffer 926. The photodetector 902 detects light that is reflected from an eye that is illuminated by an infrared laser light source controlled by the infrared laser drive and scanning optics system 904. The photodetector 902 generates a current based on the detected light.

The current-to-voltage converter 908 converts the current that is generated by the photodetector 902 into a voltage signal. The functionality of the pipelines 900 in FIG. 9 is similar to the functionality of the pipelines 800 in FIG. 8, except that the voltage signal resulting from each photodetector is split into four paths for provision to four comparators 910. The DAC 912 converts programmable digital reference voltages into respective analog reference voltages for use by the respective comparators 910. Each of the analog reference voltages is different from the other analog reference voltages. Each of the comparators 910 compares the voltage signal that is received from the photodetector 902 to the respective analog reference voltage and provides a digital state that corresponds to a difference between the voltage signal and the analog reference voltage. For instance, instead of a 1-bit analog-to-digital converter, each comparator may utilize a 2- or 3-bit analog-to-digital converter that allows for more precise amplitude information. Comparing the voltage signal for each photodetector to four different reference voltages may result in a more accurate determination of the amplitude profile of a glint, and thus can be used to accept or reject certain glints based on the voltage amplitudes and/or profiles. For example, the process may help to distinguish a specular reflection from a cornea from a specular reflection from an eyeglass or contact lens, such as by ignoring signals that match an expected voltage amplitude from eyeglasses and/or contact lenses, e.g. as determined during calibration. The use of multiple comparators also allows for the creation of a heat map of an amplitude profile for each glint.

The serializer 914 serializes the parallel signals (digital states) from the respective comparators 910 (four for each photodetector), feeding the signals from the comparators 910 in serial to the position logic 916. In other implementations, the signals may be communicated partially or fully in parallel. Corresponding interrupt handlers, as described above with regard to FIG. 8, may be triggered to capture time values associated with each glint signal and to acquire (e.g. via a MEMS trajectory calculator) synchronized signals from the MEMS scanning mirror indicating a current scan x-position and y-position of the scanning mirror by the position logic 916. The position logic 916 generates a glint list 918 with each glint having a corresponding intensity (amplitude) and x and y position of the scanning mirror. The position logic 916 determines the angle of reflection based on the position of the scanning mirror. The position logic 916 determines the location of a glint (i.e., the glint location) based on the angle of reflection.

The summing junction 920 sums the voltage signal that is received from the converter 908 with the voltage signals of other converters associated with other respective photodetectors to provide a summed analog voltage signal. The ADC 922 converts the summed analog voltage signal into a summed digital voltage signal. The gamma correction logic 924 may perform a gamma correction operation on the summed digital voltage signal to transform a luminance of linear red, green, and blue components into a nonlinear image signal. The gamma correction logic 924 provides the nonlinear image signal into the greyscale image frame buffer 926.

In the above examples, the scanning optics may include in a sine-wave mirror system that scans in a first direction (e.g. an x-direction) faster than in a second orthogonal direction (e.g. a y-direction). Due to the harmonic oscillation of the mirror, the speed of the mirror slows to a stop at the vertical and horizontal edges of the mirror motion at respective points in time, resulting in unnecessarily higher power density at the edges. As such, in some examples, sinusoidal correction may be applied to the system by turning off the infrared light source when the scanning mirror is scanning at the edges, and turning the infrared light source on when the scanning mirror is scanning between the edges. Such a correction function may further help to conserve power.

Additionally, with such a harmonically oscillating mirror system, the mirror motion has a greater speed in the center of the motion than at the edges of the motion. As such, if a constant sample rate is utilized for gaze tracking, more gaze signals are sampled at the edges of the image than in the center, resulting in variable resolution across the image. Accordingly, in some examples, the system may be configured to utilize a variable sample rate to compensate for the variable mirror speed and thus to achieve a more even resolution across the image.

Moreover, in some examples, the eye tracking laser light source may be illuminated only for sufficient time to obtain each sample and turned off between samples. This may further help to reduce power consumption by the laser and current-to-voltage converters.

It will be recognized that the pipelines 900 may not include all of the components shown in FIG. 9. Furthermore, the pipelines 900 may include components in addition to or in lieu of those shown in FIG. 9.

Figure 10:
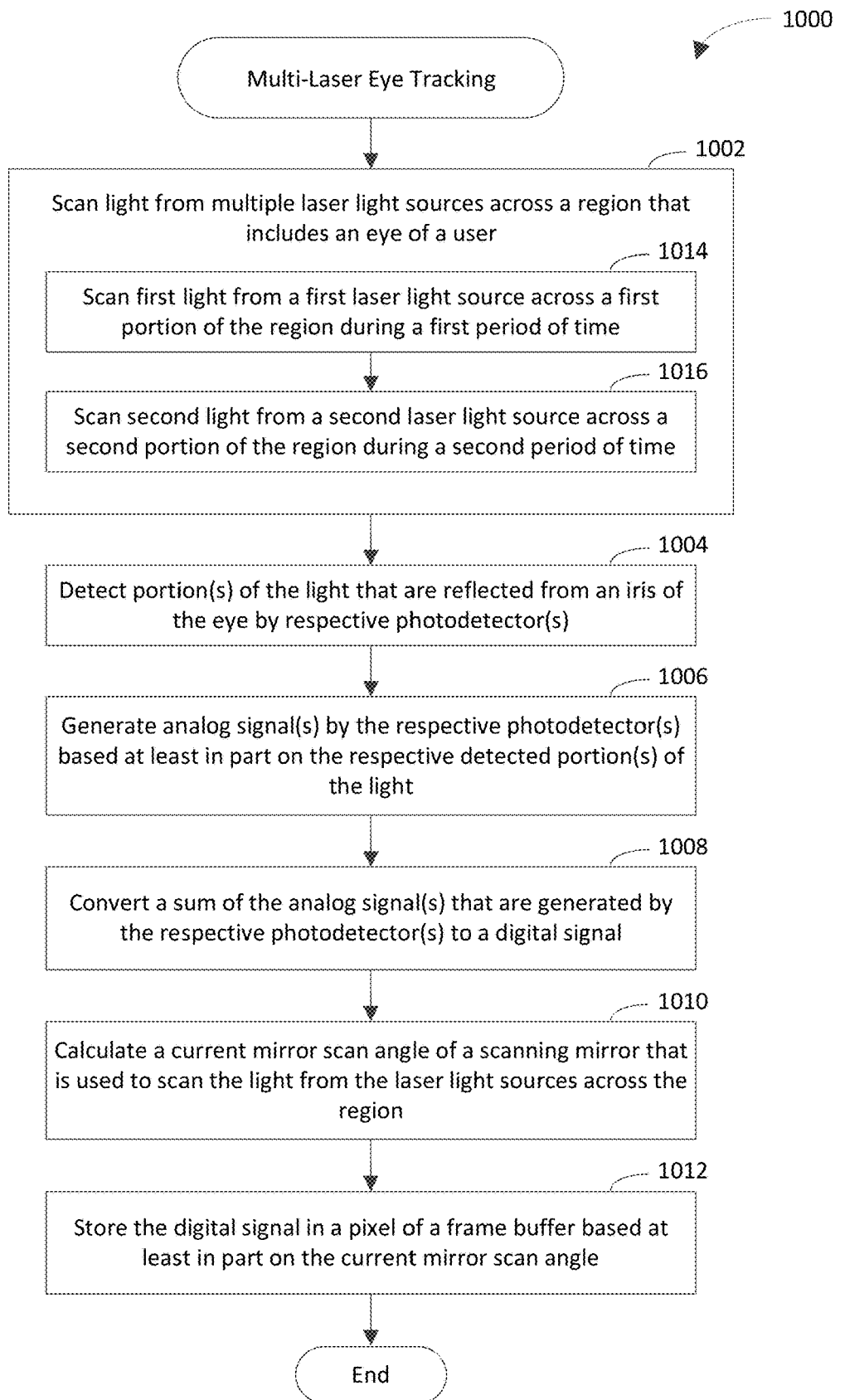
FIGS. 10-11 depict flowcharts of example methods for tracking an eye using multiple lasers in accordance with embodiments.
Figure 11:
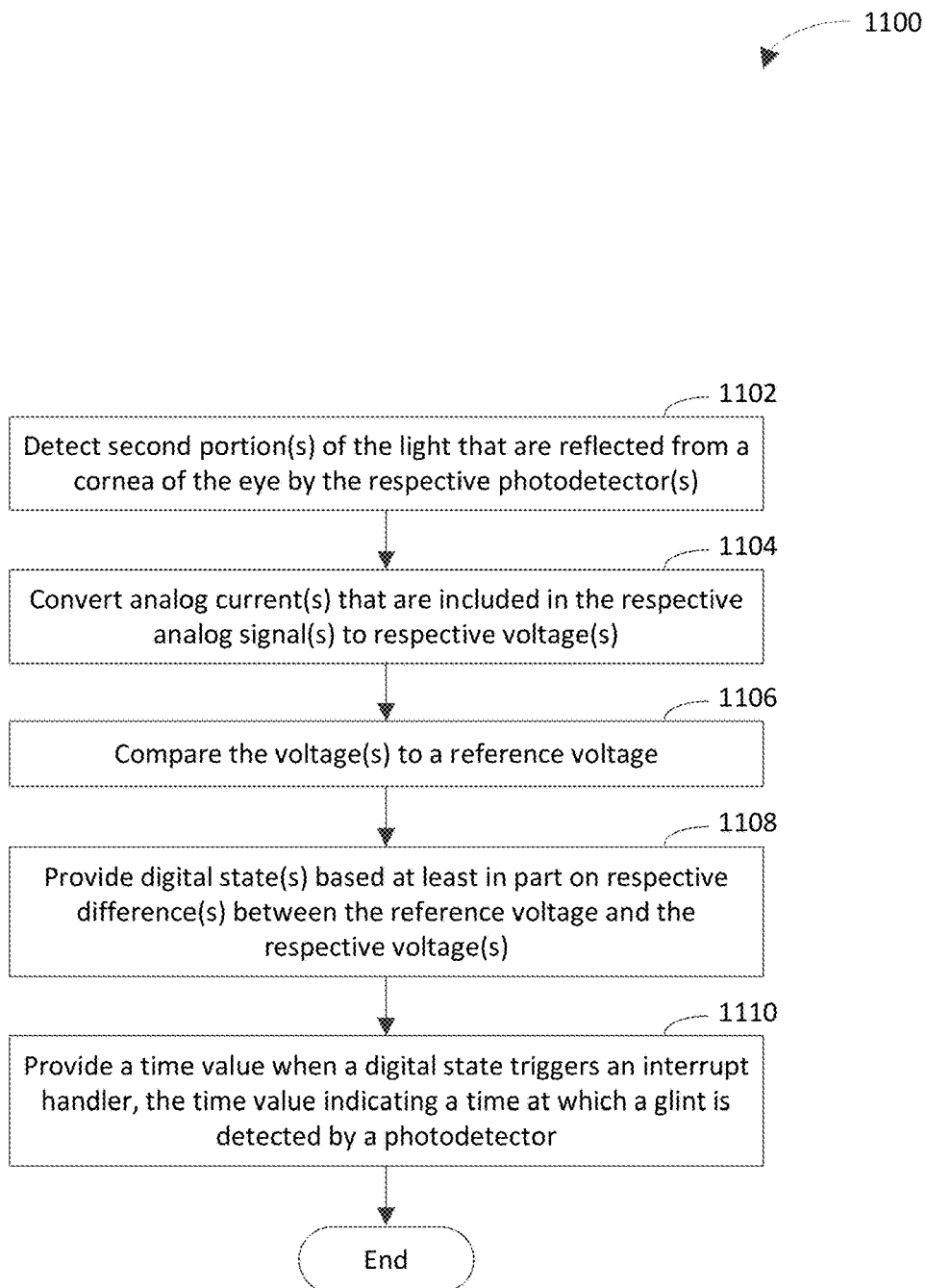
Figure 12A:
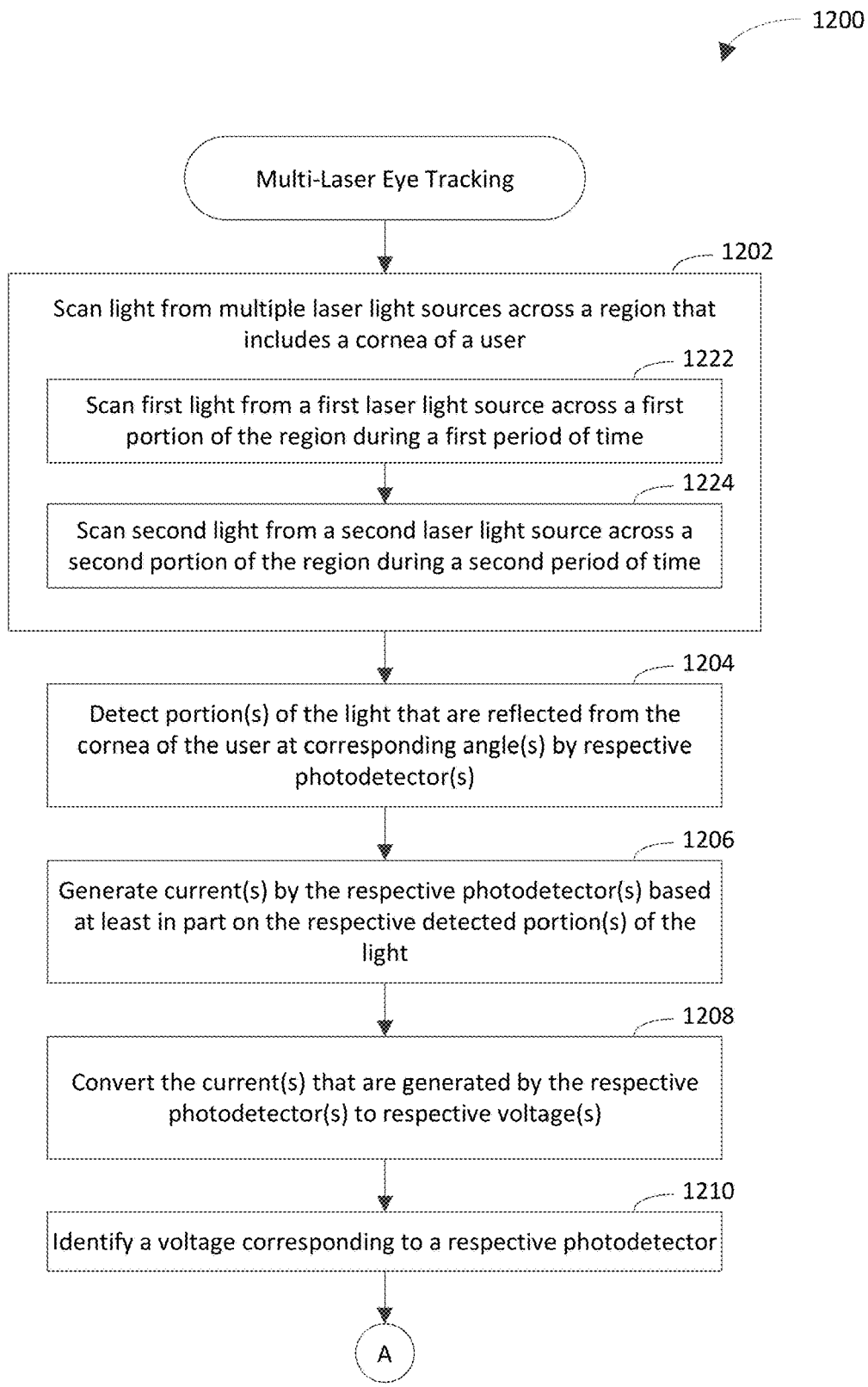
FIGS. 12A and 12B depict respective portions a flowchart of another example method for tracking an eye using multiple lasers in accordance with an embodiment.
Figure 12B:
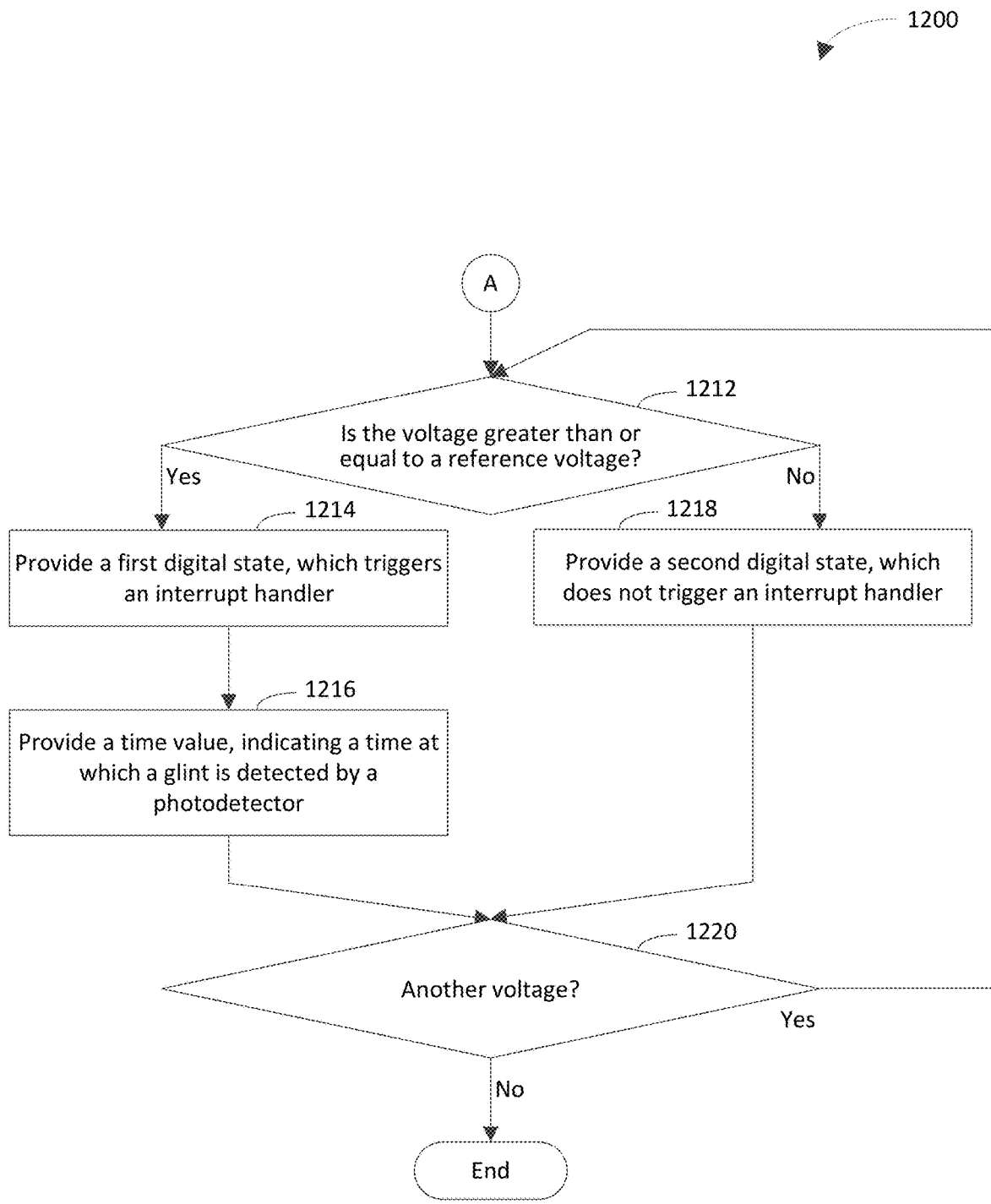

FIGS. 10 and 11 depict flowcharts 1000 and 1100 of example methods for tracking an eye using multiple lasers in accordance with embodiments. FIGS. 12A and 12B depict respective portions a flowchart 1200 of another example method for tracking an eye using multiple lasers in accordance with an embodiment. Flowcharts 1000, 1100, and 1200 may be performed by the multi-laser scanning assembly 700 shown in FIG. 7 and the processing pipelines 800 shown in FIG. 8, for example. For illustrative purposes, flowcharts 1000, 1100, and 1200 are described with respect to the multi-laser scanning assembly 700 and the processing pipelines 800. Further structural and operational embodiments will be apparent to persons skilled in the relevant art(s) based on the discussion regarding flowcharts 1000, 1100, and 1200.

As shown in FIG. 10, the method of flowchart 1000 begins at step 1002. In step 1002, light from multiple laser light sources is scanned across a region that includes an eye of a user. The light may be any suitable type of light. For instance, the light may be infrared light or ultraviolet light. In an example implementation, the scanning optics 714 scan the light from the laser diodes 710 across the region that includes the eye 806 of the user.

In an example embodiment, scanning the light from the laser light sources at step 1002 includes scanning at least a portion of the light from a first subset of the laser light sources (e.g., a first plurality of laser light sources) that is included in a first semiconductor chip. In accordance with this embodiment, scanning the light from the laser light sources at step 1002 further includes scanning at least a portion of the light from a second subset of the laser light sources (e.g., a second plurality of laser light sources) that is included in a second semiconductor chip.

In another example embodiment, scanning the light from the laser light sources at step 1002 includes scanning the light from the laser light sources that are included in a single semiconductor chip.

Step 1002 includes steps 1014 and 1016. At step 1014, first light from a first laser light source is scanned across a first portion of the region during a first period of time. At step 1016, second light from a second laser light source is scanned across a second portion of the region during a second period of time. The second portion of the region at least partially overlaps the first portion of the region. For instance, each of the first and second portions of the region may overlap a region of interest in the region across which the light is scanned. The region of interest may exclude portions of the region that do not include the eye of the user. For instance, the region of interest may exclude portions of the region that are outside an outer boundary of the eye. The second period of time is different from the first period of time. The first period of time and the second period of time may or may not overlap.

At step 1004, portion(s) of the light that are reflected from an iris of the eye are detected by respective photodetector(s). For instance, the portion(s) of the light may be reflected (e.g., scattered) from the Lambertian surface of the iris. In an example implementation, the photodetectors 804a-804d detect respective portions of the light that are reflected from the iris of the eye 806.

At step 1006, analog signal(s) are generated by the respective photodetector(s) based at least in part on the respective detected portion(s) of the light. In an example implementation, the photodetectors 804a-804d generate the respective analog currents PD1, PD2, PD3, and PD4 based at least in part on the respective detected portions of the light.

At step 1008, a sum of the analog signal(s) that are generated by the respective photodetector(s) is converted to a digital signal. In an example implementation, the ADC 816 converts a sum of the analog signals that are generated by the respective photodetectors 804a-804d to the digital signal. For example, the current-to-voltage converters 808a-808d may convert the respective analog currents PD1, PD2, PD3, and PD4 into respective analog voltages VPD1, VPD2, VPD3, and VPD4. In accordance with this embodiment, the summing junction 814 may sum the analog voltages VPD1, VPD2, VPD3, and VPD4 to provide a summed analog voltage. In further accordance with this example, the ADC 816 may convert the summed analog voltage to the digital signal.

At step 1010, a current mirror scan angle of a scanning mirror that is used to scan the light from the laser light sources across the region is calculated. In an example implementation, the MEMS trajectory calculator 818 calculates the current mirror scan angle of the scanning mirror that is used to scan the light from the laser diodes 710 across the region.

At step 1012, the digital signal is stored in a pixel of a frame buffer based at least in part on the current mirror scan angle. For instance, the digital signal may be stored in the frame buffer to produce a grayscale image of the eye of the user that captures a pupil of the eye. A location of the pupil may be derived from a lack of scattered light in an area that defines the pupil because the pupil is an aperture. Accordingly, the pupil may appear as a relatively dark spot in the grayscale image. In an example implementation, the MEMS trajectory calculator 818 stores the digital signal in a pixel of the frame buffer 820 based at leas in part on the current mirror scan angle.

In some example embodiments, one or more steps 1002, 1004, 1006, 1008, 1010, 1012, 1014, and/or 1016 of flowchart 1000 may not be performed. Moreover, steps in addition to or in lieu of steps 1002, 1004, 1006, 1008, 1010, 1012, 1014, and/or 1016 may be performed. For instance, in an example embodiment, the method of flowchart 1000 further includes determining a region of interest in the region across which the light is scanned based at least in part on a grayscale image reconstruction of the region. For example, the sequential scan control logic 712 may determine the region of interest. In accordance with this embodiment, the region of interest includes the iris of the eye, and the region of interest is smaller than the region across which the light is scanned. In further accordance with this embodiment, the method of flowchart 1000 further includes stopping the scanning of the first light from the first laser light source across the first portion of the region and beginning the scanning of the second light from the second laser light source across the second portion of the region based at least in part on a scan of the first light traversing the region of interest and reaching an outer boundary of the region of interest. For example, the first portion of the region and the second portion of the region may include the region of interest. In accordance with this example, stopping the scanning of the first light from the first laser light source across the first portion of the region and beginning the scanning of the second light from the second laser light source across the second portion of the region may cause the first light from the first laser light source and the second light from the second laser light source to be scanned across the region of interest. In an example implementation, the sequential scan control logic 712 may stop the scanning of the first light from the first laser diode D1 across the first portion of the region and begin the scanning of the second light from the second laser diode D2 across the second portion of the region based at least in part on the scan of the first light traversing the region of interest and reaching the outer boundary of the region of interest.

In another example embodiment, the method of flowchart 1000 further includes generating multiple drive signals by a multiple respective drivers. In accordance with this embodiment, the drive signals are configured to drive the respective laser light sources. For instance, the drive signals may be configured to drive the respective laser light sources sequentially during respective (e.g., consecutive and/or non-overlapping) periods of time. In an example implementation, the intensity correction logic 704 includes drivers that generate the respective drive signals to drive the respective laser diodes 710. For example, the drivers may be coupled to the respective laser diodes 710 without passing through the switch 708. In accordance with this example, the drivers may generate the respective drive signals to provide the functionality of the switch 708. For instance, rather than the switch 708 selectively coupling the DAC 706 to the laser diodes 710, the drivers may be configured to provide their drive signals one at a time so that the laser diodes 710 are illuminated sequentially.

In yet another example embodiment, the method of flowchart 1000 further includes generating multiple drive signals corresponding to multiple respective consecutive time periods by a driver. In accordance with this embodiment, the drive signals are configured to drive the respective laser light sources. For instance, the intensity correction logic 704 may include the driver that generates the drive signals to drive the respective laser diodes 710. In accordance with this embodiment, the method of flowchart 1000 further includes sequentially routing the drive signals to the respective laser light sources during the respective consecutive time periods by a multiplexer that is coupled to the driver. For instance, the drive signals may be sequentially routed to the respective laser light sources by switchably coupling the driver to the laser light sources sequentially (e.g., one-at-a-time). In an example implementation, the switch 708, which is coupled to the intensity correction logic 704, may sequentially route the drive signals to the respective laser diodes 710 during the respective consecutive time periods. In accordance with this implementation, the switch 708 may sequentially route the drive signals to the respective laser diodes 710 based on the first control signal CS1 that is received from the sequential scan control logic 712. In further accordance with this implementation, the switch 708 may sequentially route the drive signals to the respective laser diodes 710 by switchably coupling the driver to the laser diodes 710 sequentially (e.g., one-at-a-time)].

In still another example embodiment, the method of flowchart 1000 further includes modifying drive currents that are used to drive the respective laser light sources using respective compensation schemes. Each compensation scheme is configured to provide substantially uniform illumination intensity across the region for the respective laser light source by compensating for illumination intensity variations associated with a trajectory over which the light from the respective laser light source is scanned. For instance, the intensity correction logic 704 may modify the drive currents that are used to drive the respective laser diodes 710 using the respective compensation schemes.

In yet another example embodiment, the method of flowchart 1000 further includes causing an entrance pupil associated with multiple visible-light laser groupings, which are placed proximate the respective laser light sources, to be replicated over the region as the light from the laser light sources is scanned across the region. For instance, the entrance pupil may be replicated over the region concurrently with the light from the laser light sources being scanned across the region. Each visible-light laser grouping includes a red laser, a green laser, and a blue laser. In an example implementation, the scanning optics 714 cause the entrance pupil associated with the visible-light laser groupings to be replicated over the region as the light from the laser diodes 710 is scanned across the region. In accordance with this example, the visible-light laser groupings are placed proximate the respective laser diodes 710. For example, the scanning optics 714 may include a lens having first and second opposing surfaces through which the light from the laser light sources and visible light from the visible-light laser groupings passes. In accordance with this example, a distance between the first surface and the visible-light laser groupings is less than a distance between the second surface and the visible-light laser groupings. In further accordance with this example, the entrance pupil may be an optical image of a physical aperture stop associated with (e.g., included in) the scanning optics from a perspective of the visible-light laser groupings.

In still another example embodiment, the method of flowchart 1000 further includes one or more of the steps shown in flowchart 1100 of FIG. 11. As shown in FIG. 11, the method of flowchart 1100 begins at step 1102. In step 1102, second portion(s) of the light that are reflected (e.g., specularly reflected) from a cornea of the eye are detected by the respective photodetector(s). In an example implementation, the photodetectors 804a-804d detect second portions of the light that are reflected from the cornea of the eye 806. In accordance with this embodiment, generating the analog signal(s) at step 1006 includes generating the analog signal(s) by the respective photodetector(s) further based at least in part on the respective detected second portion(s) of the light. In further accordance with this embodiment, the analog signal(s) include respective analog current(s).

At step 1104, analog current(s) that are included in the respective analog signal(s) are converted to respective voltage(s). In an example implementation, the current-to-voltage converters 808a-808d convert the analog currents PD1, PD2, PD3, and PD4 into respective analog voltages VPD1, VPD2, VPD3, and VPD4.

At step 1106, the voltage(s) are compared to a reference voltage. In an example implementation, the comparators 822a-822d compare the respective analog voltages VPD1, VPD2, VPD3, and VPD4 to respective reference voltages. In accordance with this implementation, any two or more of the reference voltages may be the same or different.

At step 1108, digital state(s) are provided based at least in part on respective difference(s) between the reference voltage and the respective voltage(s). In an example implementation, the comparators 822a-822d provide respective digital states 824 based at least in part on respective differences between the respective reference voltages and the respective analog voltages VPD1, VPD2, VPD3, and VPD4.

At step 1110, a time value is provided when a digital state triggers an interrupt handler. The time value indicates a time at which a glint is detected by a photodetector. In an example implementation, an interrupt handler 826 provides a time value when a digital state triggers the interrupt handler.

As shown in FIG. 12, the method of flowchart 1200 begins at step 1202. In step 1202, light from multiple laser light sources is scanned across a region that includes a cornea of a user. The light may be any suitable type of light. For instance, the light may be infrared light or ultraviolet light. In an example implementation, the scanning optics 714 scan the light from the laser diodes 710 across the region that includes the cornea of the user.

In an example embodiment, scanning the light from the laser light sources at step 1202 includes scanning at least a portion of the light from a first subset of the laser light sources (e.g., a first plurality of laser light sources) that is included in a first semiconductor chip. In accordance with this embodiment, scanning the light from the laser light sources at step 1202 further includes scanning at least a portion of the light from a second subset of the laser light sources (e.g., a second plurality of laser light sources) that is included in a second semiconductor chip.

In another example embodiment, scanning the light from the laser light sources at step 1202 includes scanning the light from the laser light sources that are included in a single semiconductor chip.

Step 1202 includes steps 1222 and 1224. At step 1222, first light from a first laser light source is scanned across a first portion of the region during a first period of time. At step 1224, second light from a second laser light source is scanned across a second portion of the region during a second period of time. The second portion of the region at least partially overlaps the first portion of the region. For instance, each of the first and second portions of the region may overlap a region of interest in the region across which the light is scanned. The region of interest may exclude portions of the region that do not include the cornea of the user. For instance, the region of interest may exclude portions of the region that are outside an outer boundary of the cornea. The second period of time is different from the first period of time. The first period of time and the second period of time may or may not overlap.

At step 1204, portion(s) of the light that are reflected (e.g., specularly reflected) from the cornea of the user at corresponding angles(s) are detected by respective photodetector(s). In an example implementation, the photodetectors 804a-804d detect the respective portions of the light that are reflected from the cornea of the user at corresponding angles.

At step 1206, current(s) are generated by the respective photodetector(s) based at least in part on the respective detected portion(s) of the light. In an example implementation, the photodetectors 804a-804d generate the respective analog currents PD1, PD2, PD3, and PD4 based at least in part on the respective detected portions of the light.

At step 1208, the current(s) that are generated by the respective photodetector(s) are converted to respective voltage(s). In an example implementation, the current-to-voltage converters 808a-808d convert the analog currents PD1, PD2, PD3, and PD4 into respective analog voltages VPD1, VPD2, VPD3, and VPD4.

At step 1210, a voltage corresponding to a respective photodetector is identified. For instance, any of the comparators 822a-822d may identify the voltage corresponding to the respective photodetector. For instance, a first comparator 822a may identify the analog voltage VPD1 corresponding to a first photodetector 804*a*; a second comparator 822*b* may identify the analog voltage VPD2 corresponding to a second photodetector 804*b*; a third comparator 822*c* may identify the analog voltage VPD3 corresponding to a third photodetector 804*c*; or a fourth comparator 822*d* may identify the analog voltage VPD4 corresponding to a fourth photodetector 804*d*. Upon completion of step 1210, flow continued to step 1212 in FIG. 12B.

At step 1212, a determination is made whether the voltage is greater than or equal to a reference voltage. In an example implementation, the comparator (e.g., any of the comparators 822*a*-822*d*) to which the voltage corresponds determines whether the respective analog voltage VPD1, VPD2, VPD3, or VPD4 is greater than or equal to the reference voltage. If the voltage is greater than or equal to the reference voltage, flow continues to step 1214. Otherwise, flow continues to step 1218.

At step 1214, a first digital state, which triggers an interrupt handler is provided. In an example implementation, the comparator to which the voltage corresponds provides the corresponding first digital state G1, G2, G3, or G4, which triggers the interrupt handler.

At step 1216, a time value is provided. The time value indicates a time at which a glint is detected by a photodetector. In an example implementation, the interrupt handler (e.g., any of the interrupt handlers 826) that is triggered by the first digital state at step 1214 provides the time value. Upon completion of step 1216, flow continues to step 1220.

At step 1218, a second digital state, which does not trigger an interrupt handler is provided. In an example implementation, the comparator to which the voltage corresponds provides the corresponding second digital state G1, G2, G3, or G4, which does not trigger the interrupt handler.

At step 1220, a determination is made whether another voltage is to be compared to a reference voltage. If another voltage is to be compared to a reference voltage, flow returns to step 1212. Otherwise, flowchart 1200 ends. For instance, any of the comparators 822*a*-822*d* may determine whether another voltage is to be compared to a reference voltage based on whether the respective analog voltage (i.e., analog voltage VPD1, VPD2, VPD3, or VPD4) is received by the respective comparator.

In some example embodiments, one or more steps 1202, 1204, 1206, 1208, 1210, 1212, 1214, 1216, 1218, 1220, 1222, 1224, 1226, and/or 1228 of flowchart 1200 may not be performed. Moreover, steps in addition to or in lieu of steps 1202, 1204, 1206, 1208, 1210, 1212, 1214, 1216, 1218, 1220, 1222, 1224, 1226, and/or 1228 may be performed. For instance, in an example embodiment, the method of flowchart 1200 further includes determining a region of interest in the region across which the light is scanned based at least in part on a glint that is detected by a photodetector. For example, the sequential scan control logic 712 may determine the region of interest. In accordance with this embodiment, the region of interest includes the cornea of the user, and the region of interest is smaller than the region across which the light is scanned. In further accordance with this embodiment, the method of flowchart 1200 further includes stopping the scanning of the first light from the first laser light source across the first portion of the region and beginning the scanning of the second light from the second laser light source across the second portion of the region based at least in part on a scan of the first light traversing the region of interest and reaching an outer boundary of the region of interest. For instance, the first portion of the region and the second portion of the region may include the region of interest. In accordance with this example, stopping the scanning of the first light from the first laser light source across the first portion of the region and beginning the scanning of the second light from the second laser light source across the second portion of the region may cause the first light from the first laser light source and the second light from the second laser light source to be scanned across the region of interest. In an example implementation, the sequential scan control logic 712 may stop the scanning of the first light from the first laser diode D1 across the first portion of the region and begin the scanning of the second light from the second laser diode D2 across the second portion of the region based at least in part on the scan of the first light traversing the region of interest and reaching the outer boundary of the region of interest.

In another example embodiment, the method of flowchart 1200 further includes generating multiple drive signals by a multiple respective drivers. In accordance with this embodiment, the drive signals are configured to drive the respective laser light sources. For instance, the drive signals may be configured to drive the respective laser light sources sequentially during respective (e.g., consecutive and/or non-overlapping) periods of time. In an example implementation, the intensity correction logic 704 includes drivers that generate the respective drive signals to drive the respective laser diodes 710. For example, the drivers may be coupled to the respective laser diodes 710 without passing through the switch 708. In accordance with this example, the drivers may generate the respective drive signals to provide the functionality of the switch 708. For instance, rather than the switch 708 selectively coupling the DAC 706 to the laser diodes 710, the drivers may be configured to provide their drive signals one at a time so that the laser diodes 710 are illuminated sequentially.

In yet another example embodiment, the method of flowchart 1200 further includes generating multiple drive signals corresponding to multiple respective consecutive time periods by a driver. In accordance with this embodiment, the drive signals are configured to drive the respective laser light sources. For instance, the intensity correction logic 704 may include the driver that generates the drive signals to drive the respective laser diodes 710. In accordance with this embodiment, the method of flowchart 1200 further includes sequentially routing the drive signals to the respective laser light sources during the respective consecutive time periods by a multiplexer that is coupled to the driver. For instance, the drive signals may be sequentially routed to the respective laser light sources by switchably coupling the driver to the laser light sources sequentially (e.g., one-at-a-time). In an example implementation, the switch 708, which is coupled to the intensity correction logic 704, may sequentially route the drive signals to the respective laser diodes 710 during the respective consecutive time periods. In accordance with this implementation, the switch 708 may sequentially route the drive signals to the respective laser diodes 710 based on the first control signal CS1 that is received from the sequential scan control logic 712. In further accordance with this implementation, the switch 708 may sequentially route the drive signals to the respective laser diodes 710 by switchably coupling the driver to the laser diodes 710 sequentially (e.g., one-at-a-time)].

In still another example embodiment, the method of flowchart 1200 further includes modifying drive currents that are used to drive the respective laser light sources using respective compensation schemes. Each compensation scheme is configured to provide substantially uniform illumination intensity across the region for the respective laser light source by compensating for illumination intensity variations associated with a trajectory over which the light from the respective laser light source is scanned. For instance, the intensity correction logic 704 may modify the drive currents that are used to drive the respective laser diodes 710 using the respective compensation schemes.

In yet another example embodiment, the method of flowchart 1200 further includes causing an entrance pupil associated with the multiple visible-light laser groupings, which are placed proximate the respective laser light sources, to be replicated over the region as the light from the laser light sources is scanned across the region. For instance, the entrance pupil associated with the visible-light laser groupings may be replicated over the region concurrently with the light from the laser light sources being scanned across the region. Each visible-light laser grouping includes a red laser, a green laser, and a blue laser. In an example implementation, the scanning optics 714 causes the entrance pupil associated with the visible-light laser groupings to be replicated over the region as the light from the laser diodes 710 is scanned across the region. In accordance with this example, the visible-light laser groupings are placed proximate the respective laser diodes 710.

Any one or more of the intensity correction logic 704, switch 708, sequential scan control logic 712, MEMS trajectory calculator 818, gaze direction logic 828, position logic 916, gamma correction logic 924, flowchart 1000, flowchart 1100, and/or flowchart 1200 may be implemented in hardware, software, firmware, or any combination thereof.

For example, any one or more of the intensity correction logic 704, switch 708, sequential scan control logic 712, MEMS trajectory calculator 818, gaze direction logic 828, position logic 916, gamma correction logic 924, flowchart 1000, flowchart 1100, and/or flowchart 1200 may be implemented, at least in part, as computer program code configured to be executed in one or more processors.

In another example, any one or more of the intensity correction logic 704, switch 708, sequential scan control logic 712, MEMS trajectory calculator 818, gaze direction logic 828, position logic 916, gamma correction logic 924, flowchart 1000, flowchart 1100, and/or flowchart 1200 may be implemented, at least in part, as hardware logic/electrical circuitry. Such hardware logic/electrical circuitry may include one or more hardware logic components. Examples of a hardware logic component include but are not limited to a field-programmable gate array (FPGA), an application-specific integrated circuit (ASIC), an application-specific standard product (ASSP), a system-on-a-chip system (SoC), a complex programmable logic device (CPLD), etc. For instance, a SoC may include an integrated circuit chip that includes one or more of a processor (e.g., a microcontroller, microprocessor, digital signal processor (DSP), etc.), memory, one or more communication interfaces, and/or further circuits and/or embedded firmware to perform its functions.

III. Further Discussion of Some Example Embodiments

A first example multi-laser eye tracking system comprises a plurality of laser light sources, scanning optics, one or more photodetectors, an analog-to-digital converter (ADC), and one or more processors. The plurality of laser light sources includes at least a first laser light source and a second laser light source. The scanning optics are configured to scan light from the plurality of laser light sources across a region that includes an eye of a user. The scanning optics are configured to scan first light from the first laser light source across a first portion of the region during a first period of time. The scanning optics are configured to scan second light from the second laser light source across a second portion of the region during a second period of time that is different from the first period of time. The first portion of the region and the second portion of the region at least partially overlap. The one or more photodetectors are configured to generate one or more respective analog signals. Each photodetector is configured to detect a portion of the light that is reflected from an iris of the eye and configured to generate the respective analog signal based at least in part on the detected portion of the light. The ADC is configured to convert a sum of the one or more analog signals that are generated by the one or more respective photodetectors to a digital signal. The one or more processors are configured to calculate a current mirror scan angle of a scanning mirror of the scanning optics. The one or more processors are further configured to provide the digital signal into a pixel of a frame buffer based at least in part on the current mirror scan angle.

In a first aspect of the first example multi-laser eye tracking system, each photodetector is configured to detect a second portion of the light that is reflected from a cornea of the eye and configured to generate the respective analog signal further based at least in part on the detected second portion of the light. In accordance with the first aspect, the one or more analog signals include one or more respective analog currents. In further accordance with the first aspect, the first multi-laser eye tracking system further comprises one or more current-to-voltage converters configured to convert the one or more analog currents that are generated by the one or more respective photodetectors to one or more respective voltages. In further accordance with the first aspect, the first multi-laser eye tracking system further comprises one or more comparators configured to compare the one or more voltages to a reference voltage and configured to provide one or more digital states based at least in part on one or more respective differences between the reference voltage and the one or more respective voltages. In further accordance with the first aspect, the first multi-laser eye tracking system further comprises an interrupt handler configured to provide a time value when a digital state, which is included among the one or more digital states provided by the one or more comparators, triggers the interrupt handler, the time value indicating a time at which a glint is detected by a photodetector.

In a second aspect of the first example multi-laser eye tracking system, the one or more processors are further configured to determine a region of interest in the region across which the light is scanned based at least in part on a grayscale image reconstruction of the region. In accordance with the second aspect, the region of interest includes the iris of the eye and is smaller than the region across which the light is scanned. In further accordance with the second aspect, the one or more processors are further configured to control the scanning optics to stop scanning the first light from the first laser light source across the first portion of the region and to begin scanning the second light from the second laser light source across the second portion of the region based at least in part on a scan of the first light traversing the region of interest and reaching an outer boundary of the region of interest. The second aspect of the first example multi-laser eye tracking system may be implemented in combination with the first aspect of the first example multi-laser eye tracking system, though the example embodiments are not limited in this respect.

In a third aspect of the first example multi-laser eye tracking system, the first example multi-laser eye tracking system comprises a plurality of semiconductor chips that includes at least a first semiconductor chip and a second semiconductor chip. In accordance with the third aspect, the first semiconductor chip includes a first subset of the plurality of laser light sources, and the second semiconductor chip includes a second subset of the plurality of laser light sources. The third aspect of the first example multi-laser eye tracking system may be implemented in combination with the first and/or second aspect of the first example multi-laser eye tracking system, though the example embodiments are not limited in this respect.

In an example of the third aspect, the first subset includes a first plurality of laser light sources, and the second subset includes a second plurality of laser light sources.

In a fourth aspect of the first example multi-laser eye tracking system, the plurality of laser light sources are included in a single semiconductor chip. The fourth aspect of the first example multi-laser eye tracking system may be implemented in combination with the first and/or second aspect of the first example multi-laser eye tracking system, though the example embodiments are not limited in this respect.

In a fifth aspect of the first example multi-laser eye tracking system, the first example multi-laser eye tracking system further comprises a plurality of drivers configured to generate a plurality of respective drive signals, the plurality of drive signals configured to drive the plurality of respective laser light sources. The fifth aspect of the first example multi-laser eye tracking system may be implemented in combination with the first, second, third, and/or fourth aspect of the first example multi-laser eye tracking system, though the example embodiments are not limited in this respect.

In a sixth aspect of the first example multi-laser eye tracking system, the first example multi-laser eye tracking system further comprises a driver configured to generate a plurality of drive signals corresponding to a plurality of respective consecutive time periods. In accordance with the fourth aspect, the plurality of drive signals is configured to drive the plurality of respective laser light sources. In further accordance with the sixth aspect, the first example multi-laser eye tracking system further comprises a multiplexer coupled to the driver. In further accordance with the fourth aspect, the multiplexer is configured to sequentially route the plurality of drive signals to the respective laser light sources during the plurality of respective consecutive time periods. The sixth aspect of the first example multi-laser eye tracking system may be implemented in combination with the first, second, third, and/or fourth aspect of the first example multi-laser eye tracking system, though the example embodiments are not limited in this respect.

In a seventh aspect of the first example multi-laser eye tracking system, a spacing between adjacent laser light sources in the plurality of laser light sources is at least 0.1 millimeters. The seventh aspect of the first example multi-laser eye tracking system may be implemented in combination with the first, second, third, fourth, fifth, and/or sixth aspect of the first example multi-laser eye tracking system, though the example embodiments are not limited in this respect.

In an eighth aspect of the first example multi-laser eye tracking system, the one or more processors are configured to modify a plurality of drive currents that are used to drive the plurality of respective laser light sources using a plurality of respective compensation schemes, each compensation scheme configured to provide substantially uniform illumination intensity across the region for the respective laser light source by compensating for illumination intensity variations associated with a trajectory over which the light from the respective laser light source is scanned. The eighth aspect of the first example multi-laser eye tracking system may be implemented in combination with the first, second, third, fourth, fifth, sixth, and/or seventh aspect of the first example multi-laser eye tracking system, though the example embodiments are not limited in this respect.

In a ninth aspect of the first example multi-laser eye tracking system, the plurality of laser light sources are placed proximate a plurality of respective visible-light laser groupings. In accordance with the ninth aspect, each visible-light laser grouping includes a red laser, a green laser, and a blue laser. In further accordance with the ninth aspect, the scanning optics are configured to cause an entrance pupil associated with the plurality of visible-light laser groupings to be replicated over the region as the light from the plurality of laser light sources is scanned across the region. The ninth aspect of the first example multi-laser eye tracking system may be implemented in combination with the first, second, third, fourth, fifth, sixth, seventh, and/or eighth aspect of the first example multi-laser eye tracking system, though the example embodiments are not limited in this respect.

A second example multi-laser eye tracking system comprises a plurality of laser light sources, scanning optics, one or more photodetectors, one or more current-to-voltage converters, one or more comparators, and an interrupt handler. The plurality of laser light sources includes at least a first laser light source and a second laser light source. The scanning optics are configured to scan light from the plurality of laser light sources across a region that includes a cornea of a user. The scanning optics are configured to scan first light from the first laser light source across a first portion of the region during a first period of time. The scanning optics are configured to scan second light from the second laser light source across a second portion of the region during a second period of time that is different from the first period of time. The first portion of the region and the second portion of the region at least partially overlap. The one or more photodetectors are configured to generate one or more respective currents. Each photodetector is configured to detect a portion of the light that is reflected from the cornea of the user at a corresponding angle and configured to generate the respective current based at least in part on the detected portion of the light. The one or more current-to-voltage converters are configured to convert the one or more currents that are generated by the one or more respective photodetectors to one or more respective voltages. The one or more comparators are configured to compare the one or more voltages to a reference voltage and configured to provide one or more digital states based at least in part on one or more respective differences between the reference voltage and the one or more respective voltages. The interrupt handler is configured to provide a time value when a digital state, which is included among the one or more digital states provided by the one or more comparators, triggers the interrupt handler. The time value indicates a time at which a glint is detected by a photodetector.

In a first aspect of the second example multi-laser eye tracking system, the second example multi-laser eye tracking system further comprises one or more processors. The one or more processors are configured to determine a region of interest in the region across which the light is scanned based at least in part on a glint that is detected by a photodetector. In accordance with the first aspect, the region of interest includes the cornea of the user and is smaller than the region across which the light is scanned. In further accordance with the first aspect, the one or more processors are further configured to control the scanning optics to stop scanning the first light from the first laser light source across the first portion of the region and to begin scanning the second light from the second laser light source across the second portion of the region based at least in part on a scan of the first light traversing the region of interest and reaching an outer boundary of the region of interest.

In a second aspect of the second example multi-laser eye tracking system, the second example multi-laser eye tracking system comprises a plurality of semiconductor chips that includes at least a first semiconductor chip and a second semiconductor chip. In accordance with the second aspect, the first semiconductor chip includes a first subset of the plurality of laser light sources, and the second semiconductor chip includes a second subset of the plurality of laser light sources. The second aspect of the second example multi-laser eye tracking system may be implemented in combination with the first aspect of the second example multi-laser eye tracking system, though the example embodiments are not limited in this respect.

In an example of the second aspect, the first subset includes a first plurality of laser light sources, and the second subset includes a second plurality of laser light sources.

In a third aspect of the second example multi-laser eye tracking system, the plurality of laser light sources are included in a single semiconductor chip. The third aspect of the second example multi-laser eye tracking system may be implemented in combination with the first aspect of the second example multi-laser eye tracking system, though the example embodiments are not limited in this respect.

In a fourth aspect of the second example multi-laser eye tracking system, the second example multi-laser eye tracking system further comprises a plurality of drivers configured to generate a plurality of respective drive signals. In accordance with the fourth aspect, the plurality of drive signals is configured to drive the plurality of respective laser light sources. The fourth aspect of the second example multi-laser eye tracking system may be implemented in combination with the first, second, and/or third aspect of the second example multi-laser eye tracking system, though the example embodiments are not limited in this respect.

In a fifth aspect of the second example multi-laser eye tracking system, the second example multi-laser eye tracking system further comprises a driver configured to generate a plurality of drive signals corresponding to a plurality of respective consecutive time periods. In accordance with the fifth aspect, the plurality of drive signals are configured to drive the plurality of respective laser light sources. In further accordance with the fifth aspect, the second example multi-laser eye tracking system further comprises a multiplexer coupled to the driver. In further accordance with the fifth aspect, the multiplexer is configured to sequentially route the plurality of drive signals to the respective laser light sources during the plurality of respective consecutive time periods. The fifth aspect of the second example multi-laser eye tracking system may be implemented in combination with the first, second, and/or third aspect of the second example multi-laser eye tracking system, though the example embodiments are not limited in this respect.

In a sixth aspect of the second example multi-laser eye tracking system, a spacing between adjacent laser light sources in the plurality of laser light sources is at least 0.1 millimeters. The sixth aspect of the second example multi-laser eye tracking system may be implemented in combination with the first, second, third, fourth, and/or fifth aspect of the second example multi-laser eye tracking system, though the example embodiments are not limited in this respect.

In a seventh aspect of the second example multi-laser eye tracking system, the second example multi-laser eye tracking system further comprises one or more processors configured to modify a plurality of drive currents that are used to drive the plurality of respective laser light sources using a plurality of respective compensation schemes. In accordance with the seventh aspect, each compensation scheme is configured to provide substantially uniform illumination intensity across the region for the respective laser light source by compensating for illumination intensity variations associated with a trajectory over which the light from the respective laser light source is scanned. The seventh aspect of the second example multi-laser eye tracking system may be implemented in combination with the first, second, third, fourth, fifth, and/or sixth aspect of the second example multi-laser eye tracking system, though the example embodiments are not limited in this respect.

In an eighth aspect of the second example multi-laser eye tracking system, the plurality of laser light sources are placed proximate a plurality of respective visible-light laser groupings. In accordance with the eighth aspect, each visible-light laser grouping includes a red laser, a green laser, and a blue laser. In further accordance with the eighth aspect, the scanning optics are configured to cause an entrance pupil associated with the plurality of visible-light laser groupings to be replicated over the region as the light from the plurality of laser light sources is scanned across the region. The eighth aspect of the second example multi-laser eye tracking system may be implemented in combination with the first, second, third, fourth, fifth, sixth, and/or seventh aspect of the second example multi-laser eye tracking system, though the example embodiments are not limited in this respect.

In a first example method, light from a plurality of laser light sources, including at least a first laser light source and a second laser light source, is scanned across a region that includes an eye of a user. The scanning comprises scanning first light from the first laser light source across a first portion of the region during a first period of time and scanning second light from the second laser light source across a second portion of the region, which at least partially overlaps the first portion of the region, during a second period of time that is different from the first period of time. One or more portions of the light that are reflected from an iris of the eye are detected by one or more respective photodetectors. One or more analog signals are generated by the one or more respective photodetectors based at least in part on the one or more respective detected portions of the light. A sum of the one or more analog signals that are generated by the one or more respective photodetectors is converted to a digital signal. A current mirror scan angle of a scanning mirror that is used to scan the light from the plurality of laser light sources across the region is calculated. The digital signal is stored in a pixel of a frame buffer based at least in part on the current mirror scan angle.

In a first aspect of the first example method, the first example method further comprises detecting one or more second portions of the light that are reflected from a cornea of the eye by the one or more respective photodetectors. In accordance with the first aspect, generating the one or more analog signals comprises generating the one or more analog signals by the one or more respective photodetectors further based at least in part on the one or more respective detected second portions of the light. In further accordance with the first aspect, the one or more analog signals include one or more respective analog currents. In further accordance with the first aspect, the first example method further comprises converting the one or more analog currents to one or more respective voltages; comparing the one or more voltages to a reference voltage; providing one or more digital states based at least in part on one or more respective differences between the reference voltage and the one or more respective voltages; and providing a time value when a digital state, which is included among the one or more digital states, triggers an interrupt handler. In further accordance with the first aspect, the time value indicates a time at which a glint is detected by a photodetector.

In a second aspect of the first example method, the first example method comprises determining a region of interest in the region across which the light is scanned based at least in part on a grayscale image reconstruction of the region. In accordance with the second aspect, the region of interest includes the iris of the eye and is smaller than the region across which the light is scanned. In further accordance with the second aspect, the first example method comprises stopping the scanning of the first light from the first laser light source across the first portion of the region and beginning the scanning of the second light from the second laser light source across the second portion of the region based at least in part on a scan of the first light traversing the region of interest and reaching an outer boundary of the region of interest. The second aspect of the first example method may be implemented in combination with the first aspect of the first example method, though the example embodiments are not limited in this respect.

In a third aspect of the first example method, scanning the light from the plurality of laser light sources comprises scanning at least a portion of the light from a first subset of the plurality of laser light sources that is included in a first semiconductor chip. In accordance with the third aspect, scanning the light from the plurality of laser light sources comprises scanning at least a portion of the light from a second subset of the plurality of laser light sources that is included in a second semiconductor chip. The third aspect of the first example method may be implemented in combination with the first and/or second aspect of the first example method, though the example embodiments are not limited in this respect.

In an example of the third aspect, scanning at least a portion of the light from the first subset of the plurality of laser light sources comprises scanning at least a portion of the light from a first plurality of laser light sources that is included in the first subset in the first semiconductor chip. In accordance with this example, scanning at least a portion of the light from the second subset of the plurality of laser light sources comprises scanning at least a portion of the light from a second plurality of laser light sources that is included in the second subset in the second semiconductor chip.

In a fourth aspect of the first example method, scanning the light from the plurality of laser light sources comprises scanning the light from the plurality of laser light sources that are included in a single semiconductor chip. The fourth aspect of the first example method may be implemented in combination with the first and/or second aspect of the first example method, though the example embodiments are not limited in this respect.

In a fifth aspect of the first example method, the first example method further comprises generating a plurality of drive signals by a plurality of respective drivers, the plurality of drive signals configured to drive the plurality of respective laser light sources. The fifth aspect of the first example method may be implemented in combination with the first, second, third, and/or fourth aspect of the first example method, though the example embodiments are not limited in this respect.

In a sixth aspect of the first example method, the first example method further comprises generating a plurality of drive signals corresponding to a plurality of respective consecutive time periods by a driver. In accordance with this sixth aspect, the plurality of drive signals is configured to drive the plurality of respective laser light sources. In further accordance with the sixth aspect, the first example method further comprises sequentially routing the plurality of drive signals to the respective laser light sources during the plurality of respective consecutive time periods by a multiplexer that is coupled to the driver. The sixth aspect of the first example method may be implemented in combination with the first, second, third, and/or fourth aspect of the first example method, though the example embodiments are not limited in this respect.

In a seventh aspect of the first example method, a spacing between adjacent laser light sources in the plurality of laser light sources is at least 0.1 millimeters. The seventh aspect of the first example method may be implemented in combination with the first, second, third, fourth, fifth, and/or sixth aspect of the first example method, though the example embodiments are not limited in this respect.

In an eighth aspect of the first example method, the first example method further comprises modifying a plurality of drive currents that are used to drive the plurality of respective laser light sources using a plurality of respective compensation schemes, each compensation scheme configured to provide substantially uniform illumination intensity across the region for the respective laser light source by compensating for illumination intensity variations associated with a trajectory over which the light from the respective laser light source is scanned. The eighth aspect of the first example method may be implemented in combination with the first, second, third, fourth, fifth, sixth, and/or seventh aspect of the first example method, though the example embodiments are not limited in this respect.

In a ninth aspect of the first example method, the first example method further comprises scanning visible light from a plurality of visible-light laser groupings, which are placed proximate the plurality of respective laser light sources, across the region as the light from the plurality of laser light sources is scanned across the region. In accordance with the ninth aspect, each visible-light laser grouping includes a red laser, a green laser, and a blue laser. The ninth aspect of the first example method may be implemented in combination with the first, second, third, fourth, fifth, sixth, seventh, and/or eighth aspect of the first example method, though the example embodiments are not limited in this respect.

In a second example method light from a plurality of laser light sources, including at least a first laser light source and a second laser light source, is scanned across a region that includes a cornea of a user. The scanning comprises scanning first light from the first laser light source across a first portion of the region during a first period of time and scanning second light from the second laser light source across a second portion of the region, which at least partially overlaps the first portion of the region, during a second period of time that is different from the first period of time. One or more portions of the light that are reflected from the cornea of the user at one or more respective corresponding angles are detected by one or more respective photodetectors. One or more currents are generated by the one or more respective photodetectors based at least in part on the one or more respective detected portions of the light. The one or more currents that are generated by the one or more respective photodetectors are converted to one or more respective voltages. The one or more voltages are compared to a reference voltage. One or more digital states are provided based at least in part on one or more respective differences between the reference voltage and the one or more respective voltages. A time value is provided when a digital state, which is included among the one or more digital states, triggers an interrupt handler. The time value indicates a time at which a glint is detected by a photodetector.

In a first aspect of the second example method, the second example method comprises determining a region of interest in the region across which the light is scanned based at least in part on a glint that is detected by a photodetector. In accordance with the first aspect, the region of interest includes the cornea of the user and is smaller than the region across which the light is scanned. In further accordance with the first aspect, the second example method comprises stopping the scanning of the first light from the first laser light source across the first portion of the region and beginning the scanning of the second light from the second laser light source across the second portion of the region based at least in part on a scan of the first light traversing the region of interest and reaching an outer boundary of the region of interest.

In a second aspect of the second example method, scanning the light from the plurality of laser light sources comprises scanning at least a portion of the light from a first subset of the plurality of laser light sources that is included in a first semiconductor chip and scanning at least a portion of the light from a second subset of the plurality of laser light sources that is included in a second semiconductor chip. The second aspect of the second example method may be implemented in combination with the first aspect of the second example method, though the example embodiments are not limited in this respect.

In an example of the second aspect, scanning at least a portion of the light from the first subset of the plurality of laser light sources comprises scanning at least a portion of the light from a first plurality of laser light sources that is included in the first subset in the first semiconductor chip. In accordance with this example, scanning at least a portion of the light from the second subset of the plurality of laser light sources comprises scanning at least a portion of the light from a second plurality of laser light sources that is included in the second subset in the second semiconductor chip.

In a third aspect of the second example method, scanning the light from the plurality of laser light sources comprises scanning the light from the plurality of laser light sources that are included in a single semiconductor chip. The third aspect of the second example method may be implemented in combination with the first aspect of the second example method, though the example embodiments are not limited in this respect.

In a fourth aspect of the second example method, the second example method further comprises generating a plurality of drive signals by a plurality of respective drivers. In accordance with the fourth aspect, the plurality of drive signals is configured to drive the plurality of respective laser light sources. The fourth aspect of the second example method may be implemented in combination with the first, second, and/or third aspect of the second example method, though the example embodiments are not limited in this respect.

In a fifth aspect of the second example method, the second example method further comprises generating a plurality of drive signals corresponding to a plurality of respective consecutive time periods by a driver. In accordance with the fifth aspect, the plurality of drive signals is configured to drive the plurality of respective laser light sources. In further accordance with the fifth aspect, the second example method further comprises sequentially routing the plurality of drive signals to the respective laser light sources during the plurality of respective consecutive time periods by a multiplexer that is coupled to the driver. The fifth aspect of the second example method may be implemented in combination with the first, second, and/or third aspect of the second example method, though the example embodiments are not limited in this respect.

In a sixth aspect of the second example method, a spacing between adjacent laser light sources in the plurality of laser light sources is at least 0.1 millimeters. The sixth aspect of the second example method may be implemented in combination with the first, second, third, fourth, and/or fifth aspect of the second example method, though the example embodiments are not limited in this respect.

In a seventh aspect of the second example method, the second example method further comprises modifying a plurality of drive currents that are used to drive the plurality of respective laser light sources using a plurality of respective compensation schemes. In accordance with the seventh aspect, each compensation scheme is configured to provide substantially uniform illumination intensity across the region for the respective laser light source by compensating for illumination intensity variations associated with a trajectory over which the light from the respective laser light source is scanned. The seventh aspect of the second example method may be implemented in combination with the first, second, third, fourth, fifth, and/or sixth aspect of the second example method, though the example embodiments are not limited in this respect.

In an eighth aspect of the second example method, the second example method further comprises scanning visible light from a plurality of visible-light laser groupings, which are placed proximate the plurality of respective laser light sources, across the region as the light from the plurality of laser light sources is scanned across the region. In accordance with the eighth aspect, each visible-light laser grouping includes a red laser, a green laser, and a blue laser. The eighth aspect of the second example method may be implemented in combination with the first, second, third, fourth, fifth, sixth, and/or seventh aspect of the second example method, though the example embodiments are not limited in this respect.

A first example computer program product comprises a computer-readable storage medium having instructions recorded thereon for enabling a processor-based system to perform operations. The operations comprise cause light from a plurality of laser light sources, including at least a first laser light source and a second laser light source, to be scanned across a region that includes an eye of a user, comprising cause first light from the first laser light source to be scanned across a first portion of the region during a first period of time and cause second light from the second laser light source to be scanned across a second portion of the region, which at least partially overlaps the first portion of the region, during a second period of time that is different from the first period of time. The operations further comprise calculate a current mirror scan angle of a scanning mirror that is used to scan the light from the plurality of laser light sources across the region. The operations further comprise cause a digital signal, which is converted from a sum of one or more analog signals that are generated by one or more respective photodetectors based at least in part on one or more respective portions of the light that are reflected from an iris of the eye, to be provided into a pixel of a frame buffer based at least in part on the current mirror scan angle.

A second example computer program product comprises a computer-readable storage medium having instructions recorded thereon for enabling a processor-based system to perform operations. The operations comprise cause light from a plurality of laser light sources, including at least a first laser light source and a second laser light source, to be scanned across a region that includes a cornea of a user, comprising cause first light from the first laser light source to be scanned across a first portion of the region during a first period of time and cause second light from the second laser light source to be scanned across a second portion of the region, which at least partially overlaps the first portion of the region, during a second period of time that is different from the first period of time. The operations further comprise cause one or more voltages, which are converted from one or more respective currents that are generated by one or more respective photodetectors based at least in part on one or more respective portions of the light that are reflected from the cornea of the user at one or more respective corresponding angles, to be compared to a reference voltage. The operations further comprise provide one or more digital states based at least in part on one or more respective differences between the reference voltage and the one or more respective voltages. The operations further comprise provide a time value when a digital state, which is included among the one or more digital states, triggers an interrupt handler. The time value indicates a time at which a glint is detected by a photodetector.

IV. Example Computer System

Figure 13:
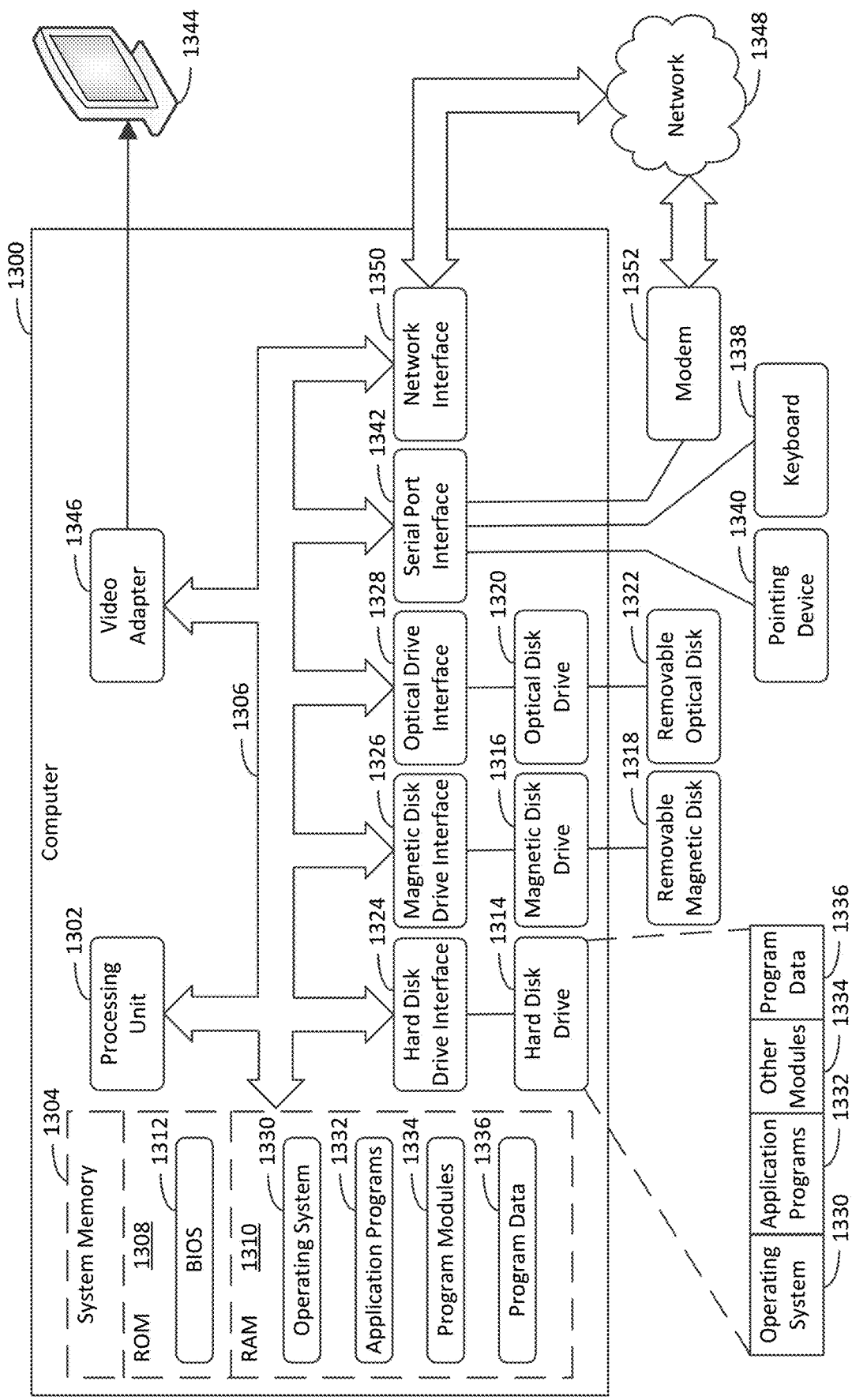
FIG. 13 depicts an example computer in which embodiments may be implemented.

FIG. 13 depicts an example computer 1300 in which embodiments may be implemented. The multi-laser scanning assembly 700, the pipelines 800, and/or the pipelines 900 may be implemented using computer 1300, including one or more features of computer 1300 and/or alternative features. Computer 1300 may be a general-purpose computing device in the form of a conventional personal computer, a mobile computer, or a workstation, for example, or computer 1300 may be a special purpose computing device. For instance, computer 1300 may be a desktop computer, a laptop computer, a tablet computer, a wearable computer such as a smart watch or a head-mounted computer, a personal digital assistant, a cellular telephone, an Internet of things (IoT) device, or the like. The description of computer 1300 provided herein is provided for purposes of illustration, and is not intended to be limiting. Embodiments may be implemented in further types of computer systems, as would be known to persons skilled in the relevant art(s).

As shown in FIG. 13, computer 1300 includes a processing unit 1302, a system memory 1304, and a bus 1306 that couples various system components including system memory 1304 to processing unit 1302. Bus 1306 represents one or more of any of several types of bus structures, including a memory bus or memory controller, a peripheral bus, an accelerated graphics port, and a processor or local bus using any of a variety of bus architectures. System memory 1304 includes read only memory (ROM) 1308 and random access memory (RAM) 1310. A basic input/output system 1312 (BIOS) is stored in ROM 1308.

Computer 1300 also has one or more of the following drives: a hard disk drive 1314 for reading from and writing to a hard disk, a magnetic disk drive 1316 for reading from or writing to a removable magnetic disk 1318, and an optical disk drive 1320 for reading from or writing to a removable optical disk 1322 such as a CD ROM, DVD ROM, or other optical media. Hard disk drive 1314, magnetic disk drive 1316, and optical disk drive 1320 are connected to bus 1306 by a hard disk drive interface 1324, a magnetic disk drive interface 1326, and an optical drive interface 1328, respectively. The drives and their associated computer-readable storage media provide nonvolatile storage of computer-readable instructions, data structures, program modules and other data for the computer. Although a hard disk, a removable magnetic disk and a removable optical disk are described, other types of computer-readable storage media can be used to store data, such as flash memory cards, digital video disks, random access memories (RAMs), read only memories (ROM), and the like.

A number of program modules may be stored on the hard disk, magnetic disk, optical disk, ROM, or RAM. These programs include an operating system 1330, one or more application programs 1332, other program modules 1334, and program data 1336. Application programs 1332 or program modules 1334 may include, for example, computer program logic for implementing any one or more of the intensity correction logic 704, switch 708, sequential scan control logic 712, MEMS trajectory calculator 818, gaze direction logic 828, position logic 916, gamma correction logic 924, flowchart 1000 (including any step of flowchart 1000), flowchart 1100 (including any step of flowchart 1100), and/or flowchart 1200 (including any step of flowchart 1200), as described herein.

A user may enter commands and information into the computer 1300 through input devices such as keyboard 1338 and pointing device 1340. Other input devices (not shown) may include a microphone, joystick, game pad, satellite dish, scanner, touch screen, camera, accelerometer, gyroscope, or the like. These and other input devices are often connected to the processing unit 1302 through a serial port interface 1342 that is coupled to bus 1306, but may be connected by other interfaces, such as a parallel port, game port, or a universal serial bus (USB).

A display device 1344 (e.g., a monitor) is also connected to bus 1306 via an interface, such as a video adapter 1346. In addition to display device 1344, computer 1300 may include other peripheral output devices (not shown) such as speakers and printers.

Computer 1300 is connected to a network 1348 (e.g., the Internet) through a network interface or adapter 1350, a modem 1352, or other means for establishing communications over the network. Modem 1352, which may be internal or external, is connected to bus 1306 via serial port interface 1342.

As used herein, the terms "computer program medium" and "computer-readable storage medium" are used to generally refer to media (e.g., non-transitory media) such as the hard disk associated with hard disk drive 1314, removable magnetic disk 1318, removable optical disk 1322, as well as other media such as flash memory cards, digital video disks, random access memories (RAMs), read only memories (ROM), and the like. Such computer-readable storage media are distinguished from and non-overlapping with communication media (do not include communication media). Communication media embodies computer-readable instructions, data structures, program modules or other data in a modulated data signal such as a carrier wave. The term "modulated data signal" means a signal that has one or more of its characteristics set or changed in such a manner as to encode information in the signal. By way of example, and not limitation, communication media includes wireless media such as acoustic, RF, infrared and other wireless media, as well as wired media. Example embodiments are also directed to such communication media.

As noted above, computer programs and modules (including application programs 1332 and other program modules 1334) may be stored on the hard disk, magnetic disk, optical disk, ROM, or RAM. Such computer programs may also be received via network interface 1350 or serial port interface 1342. Such computer programs, when executed or loaded by an application, enable computer 1300 to implement features of embodiments discussed herein. Accordingly, such computer programs represent controllers of the computer 1300.

Example embodiments are also directed to computer program products comprising software (e.g., computer-readable instructions) stored on any computer-useable medium. Such software, when executed in one or more data processing devices, causes data processing device(s) to operate as described herein. Embodiments may employ any computer-useable or computer-readable medium, known now or in the future. Examples of computer-readable mediums include, but are not limited to storage devices such as RAM, hard drives, floppy disks, CD ROMs, DVD ROMs, zip disks, tapes, magnetic storage devices, optical storage devices, MEMS-based storage devices, nanotechnology-based storage devices, and the like.

It will be recognized that the disclosed technologies are not limited to any particular computer or type of hardware. Certain details of suitable computers and hardware are well known and need not be set forth in detail in this disclosure.

V. Conclusion

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims, and other equivalent features and acts are intended to be within the scope of the claims.

What is claimed is:

1. A multi-laser eye tracking system comprising:
a plurality of laser light sources that includes at least a first laser light source and a second laser light source;
scanning optics configured to scan light from the plurality of laser light sources across a region that includes a cornea of a user, the scanning optics configured to scan first light from the first laser light source across a first portion of the region during a first period of time, the scanning optics configured to scan second light from the second laser light source across a second portion of the region during a second period of time that is different from the first period of time, the first portion of the region and the second portion of the region at least partially overlapping;
a photodetector configured to detect a portion of the light that is reflected from the cornea of the user at a corresponding angle to provide a detected portion of the light and further configured to generate a current based at least on the detected portion of the light;
a current-to-voltage converter configured to convert the current that is generated by the photodetector to a voltage;
a comparator configured to compare the voltage to a reference voltage and further configured to provide a digital state based at least on a difference between the reference voltage and the voltage; and
an interrupt handler configured to provide a time value when the digital state, which is provided by the comparator, triggers the interrupt handler, the time value indicating a time at which a glint is detected by the photodetector.

2. The multi-laser eye tracking system of claim 1, further comprising a processing system configured to:
determine a region of interest in the region across which the light is scanned based at least on the glint that is detected by the photodetector, wherein the region of interest includes the cornea of the user and is smaller than the region across which the light is scanned; and
control the scanning optics to stop scanning the first light from the first laser light source across the first portion of the region and to begin scanning the second light from the second laser light source across the second portion of the region based at least on a scan of the first light traversing the region of interest and reaching an outer boundary of the region of interest.

3. The multi-laser eye tracking system of claim 1, comprising a plurality of semiconductor chips that includes at least a first semiconductor chip and a second semiconductor chip, the first semiconductor chip including a first subset of the plurality of laser light sources, the second semiconductor chip including a second subset of the plurality of laser light sources.

4. The multi-laser eye tracking system of claim 3, wherein the first subset includes a first plurality of laser light sources; and
wherein the second subset includes a second plurality of laser light sources.

5. The multi-laser eye tracking system of claim 1, wherein the plurality of laser light sources are included in a single semiconductor chip.

6. The multi-laser eye tracking system of claim 1, further comprising:
a plurality of drivers configured to generate a plurality of respective drive signals, the plurality of drive signals configured to drive the plurality of respective laser light sources.

7. The multi-laser eye tracking system of claim 1, further comprising:
a driver configured to generate a plurality of drive signals corresponding to a plurality of respective consecutive time periods, the plurality of drive signals configured to drive the plurality of respective laser light sources; and
a multiplexer coupled to the driver, the multiplexer configured to sequentially route the plurality of drive signals to the respective laser light sources during the plurality of respective consecutive time periods.

8. The multi-laser eye tracking system of claim 1, further comprising:
a processing system configured to modify a plurality of drive currents that are used to drive the plurality of respective laser light sources using a plurality of respective compensation schemes, each compensation scheme configured to provide substantially uniform illumination intensity across the region for the respective laser light source by compensating for illumination intensity variations associated with a trajectory over which the light from the respective laser light source is scanned.

9. The multi-laser eye tracking system of claim 1, wherein the plurality of laser light sources are placed proximate a plurality of respective visible-light laser groupings, each visible-light laser grouping including a red laser, a green laser, and a blue laser; and wherein the scanning optics are configured to cause an entrance pupil associated with the plurality of visible-light laser groupings to be replicated over the region as the light from the plurality of laser light sources is scanned across the region.

10. A method comprising:

scanning light from a plurality of laser light sources, including at least a first laser light source and a second laser light source, across a region that includes a cornea of a user, the scanning comprising:

scanning first light from the first laser light source across a first portion of the region during a first period of time; and scanning second light from the second laser light source across a second portion of the region, which at least partially overlaps the first portion of the region, during a second period of time that is different from the first period of time;

detecting a portion of the light that is reflected from the cornea of the user at a corresponding angle by a photodetector to provide a detected portion of the light;

generating a current by the photodetector based at least on the detected portion of the light;

converting the current that is generated by the photodetector to a voltage;

providing a digital state based at least on a difference between the voltage and a reference voltage; and providing a time value when the digital state triggers an interrupt handler, the time value indicating a time at which a glint is detected by the photodetector.

11. The method of claim 10, comprising:

determining a region of interest in the region across which the light is scanned based at least on the glint that is detected by the photodetector, wherein the region of interest includes the cornea of the user and is smaller than the region across which the light is scanned; and stopping the scanning of the first light from the first laser light source across the first portion of the region and beginning the scanning of the second light from the second laser light source across the second portion of the region based at least on a scan of the first light traversing the region of interest and reaching an outer boundary of the region of interest.

12. The method of claim 10, wherein scanning the light from the plurality of laser light sources comprises:

scanning at least a portion of the light from a first subset of the plurality of laser light sources that is included in a first semiconductor chip; and scanning at least a portion of the light from a second subset of the plurality of laser light sources that is included in a second semiconductor chip.

13. The method of claim 12, wherein scanning at least a portion of the light from the first subset of the plurality of laser light sources comprises:

scanning at least a portion of the light from a first plurality of laser light sources that is included in the first subset in the first semiconductor chip; and wherein scanning at least a portion of the light from the second subset of the plurality of laser light sources comprises:

scanning at least a portion of the light from a second plurality of laser light sources that is included in the second subset in the second semiconductor chip.

14. The method of claim 10, wherein scanning the light from the plurality of laser light sources comprises:

scanning the light from the plurality of laser light sources that are included in a single semiconductor chip.

15. The method of claim 10, further comprising:

generating a plurality of drive signals by a plurality of respective drivers, wherein the plurality of drive signals is configured to drive the plurality of respective laser light sources.

16. The method of claim 10, further comprising:

generating a plurality of drive signals corresponding to a plurality of respective consecutive time periods by a driver, wherein the plurality of drive signals is configured to drive the plurality of respective laser light sources; and sequentially routing the plurality of drive signals to the respective laser light sources during the plurality of respective consecutive time periods by a multiplexer that is coupled to the driver.

17. The method of claim 10, wherein a spacing between adjacent laser light sources in the plurality of laser light sources is at least 0.1 millimeters.

18. The method of claim 10, further comprising:

modifying a plurality of drive currents that are used to drive the plurality of respective laser light sources using a plurality of respective compensation schemes, wherein each compensation scheme is configured to provide substantially uniform illumination intensity across the region for the respective laser light source by compensating for illumination intensity variations associated with a trajectory over which the light from the respective laser light source is scanned.

19. The method of claim 10, further comprising:

scanning visible light from a plurality of visible-light laser groupings, which are placed proximate the plurality of respective laser light sources, across the region as the light from the plurality of laser light sources is scanned across the region, wherein each visible-light laser grouping includes a red laser, a green laser, and a blue laser.

20. A computer program product comprising a computer-readable storage medium, which is not a signal, having instructions recorded thereon for enabling a processor-based system to perform operations, the operations comprise:

causing light from a plurality of laser light sources, including at least a first laser light source and a second laser light source, to be scanned across a region that includes a cornea of a user, comprising:

causing first light from the first laser light source to be scanned across a first portion of the region during a first period of time; and causing second light from the second laser light source to be scanned across a second portion of the region, which at least partially overlaps the first portion of the region, during a second period of time that is different from the first period of time;

causing a voltage, which is converted from a current that is generated by a photodetector based at least on a portion of the light that is reflected from the cornea of the user at a corresponding angle, to be compared to a reference voltage;

providing a digital state based at least on a difference between the reference voltage and the voltage; and providing a time value when the digital state triggers an interrupt handler, wherein the time value indicates a time at which a glint is detected by the photodetector.

* * * * *